(12) United States Patent
Viola et al.

(10) Patent No.: US 8,226,667 B2
(45) Date of Patent: Jul. 24, 2012

(54) AXIAL STITCHING DEVICE

(75) Inventors: Frank J. Viola, Sandy Hook, CT (US); Eric J. Taylor, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 559 days.

(21) Appl. No.: 12/442,898

(22) PCT Filed: Oct. 4, 2007

(86) PCT No.: PCT/US2007/021482
§ 371 (c)(1),
(2), (4) Date: Mar. 25, 2009

(87) PCT Pub. No.: WO2008/045376
PCT Pub. Date: Apr. 17, 2008

(65) Prior Publication Data
US 2010/0030239 A1 Feb. 4, 2010

Related U.S. Application Data

(60) Provisional application No. 60/849,562, filed on Oct. 5, 2006, provisional application No. 60/849,508, filed on Oct. 5, 2006, provisional application No. 60/923,804, filed on Apr. 16, 2007.

(51) Int. Cl.
*A61B 17/04* (2006.01)
(52) U.S. Cl. .................................. 606/144; 606/148
(58) Field of Classification Search .................. 606/144, 606/148, 205, 207, 208, 213, 147, 145; 604/411
See application file for complete search history.

(56) References Cited

U.S. PATENT DOCUMENTS

| 5,389,103 A * | 2/1995 | Melzer et al. ................ 606/144 |
| 5,931,855 A | 8/1999 | Buncke |
| 2005/0165419 A1 * | 7/2005 | Sauer et al. .................. 606/148 |

OTHER PUBLICATIONS

International Search Report for PCT/US07/021482 date of completion is Feb. 25, 2008 (2 pages).

* cited by examiner

*Primary Examiner* — Corrine M McDermott
*Assistant Examiner* — Christina Lauer

(57) ABSTRACT

An endoscopic stitching device is provided including an end effector configured and adapted to perform at least a pair of functions; and a single actuation cable operatively connected to the end effector, wherein the actuation cable is capable of effecting operation of at least the pair of functions. The actuation cable is capable of effecting a first operation of the pair of functions upon an axial translation thereof, and a second operation of the pair of functions upon a rotation thereof.

21 Claims, 26 Drawing Sheets

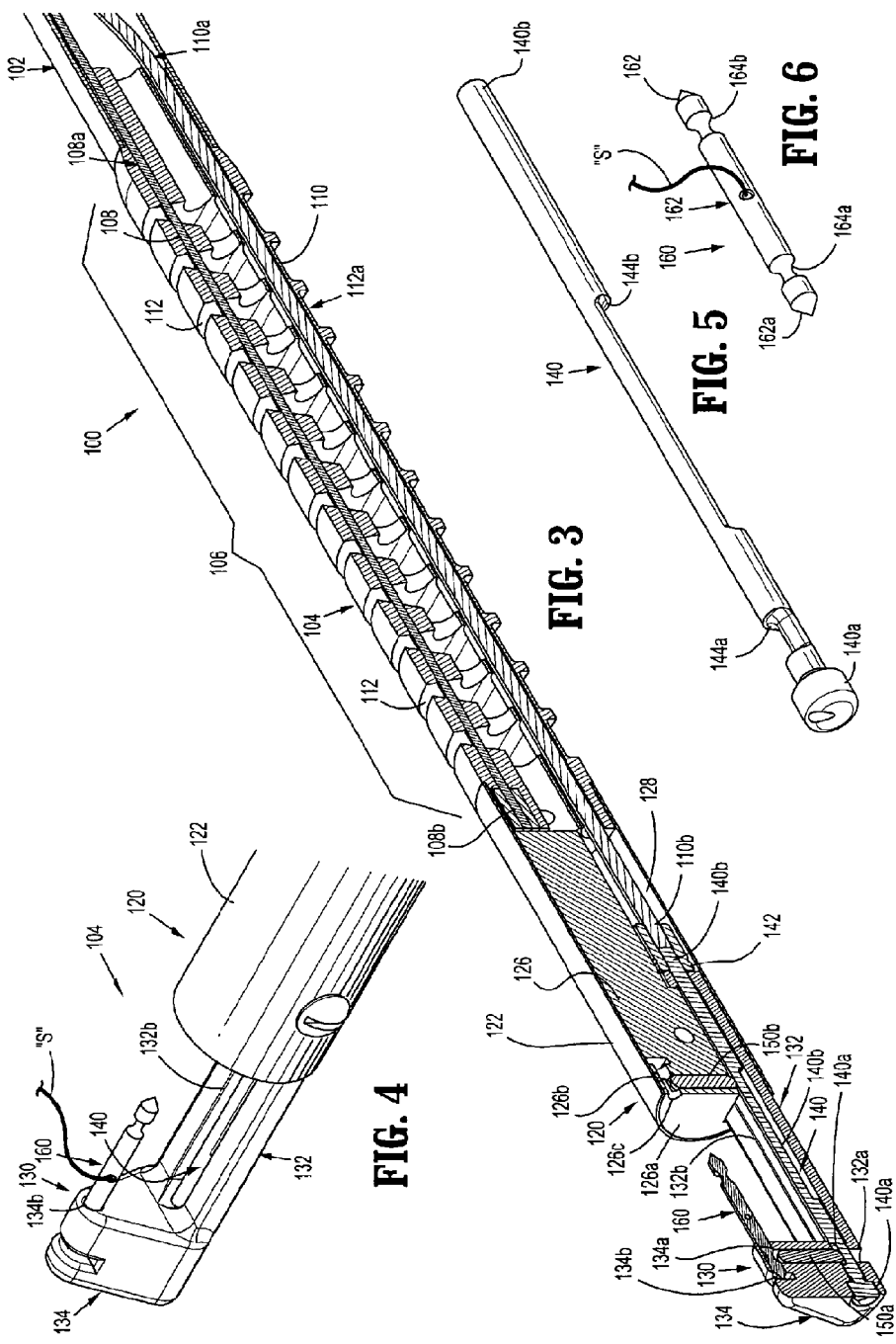

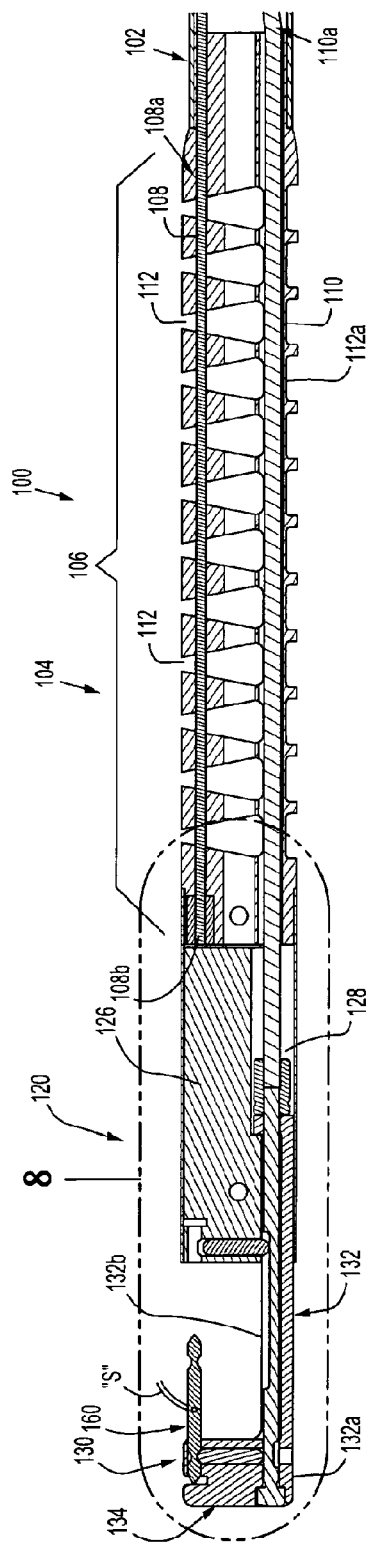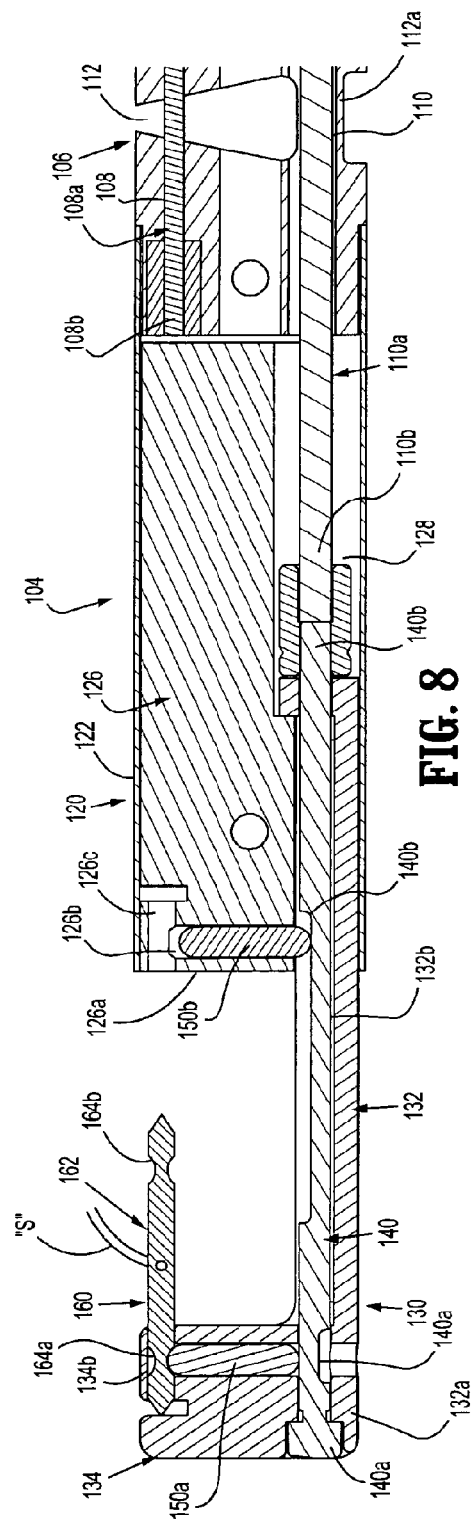
FIG. 7
FIG. 8

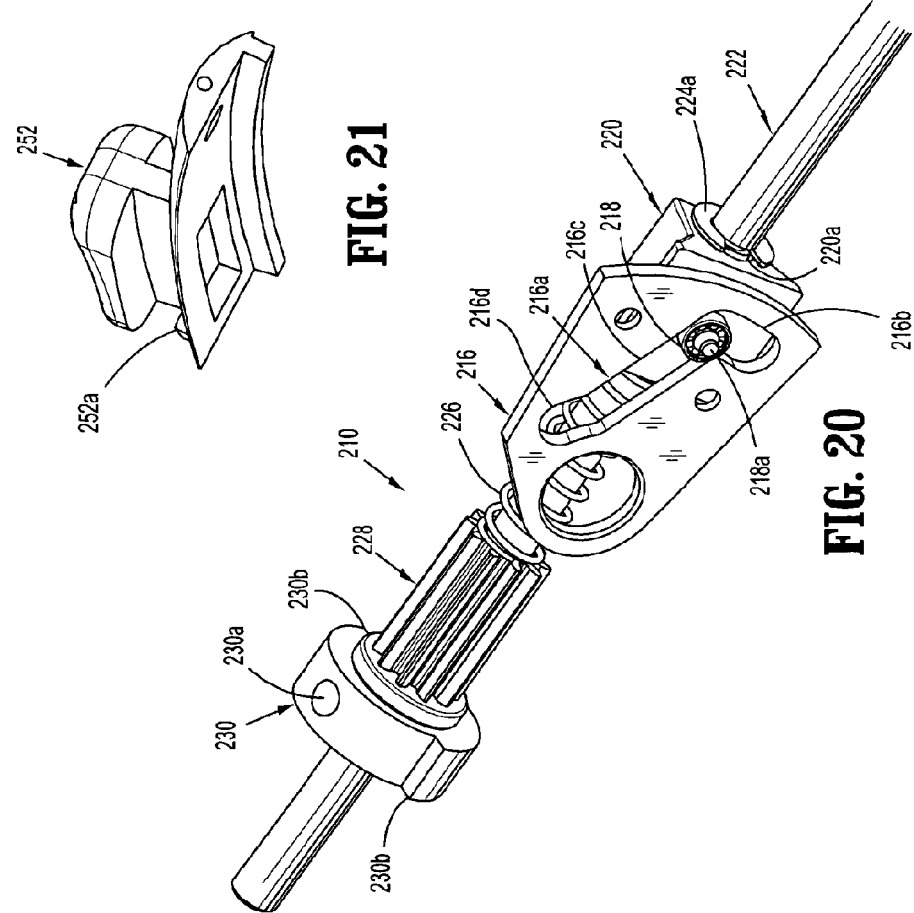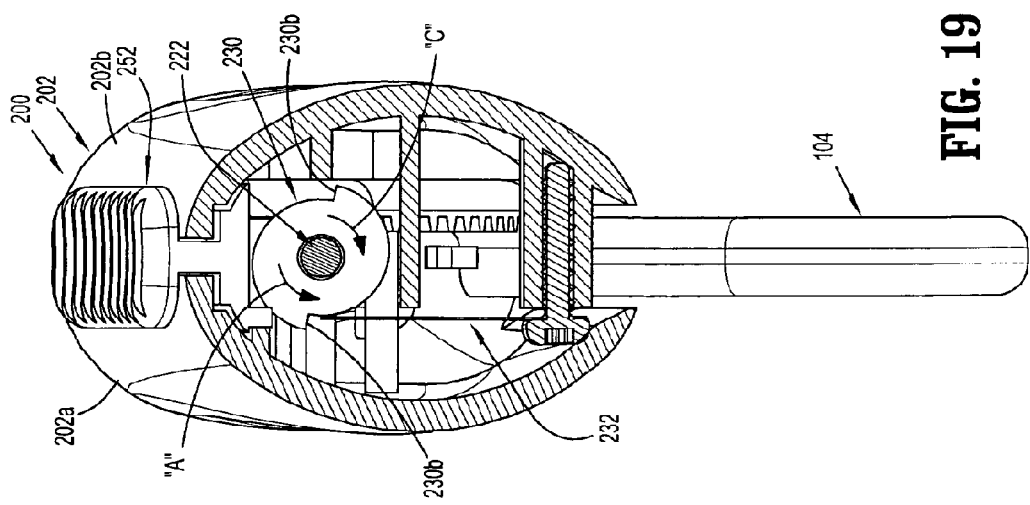

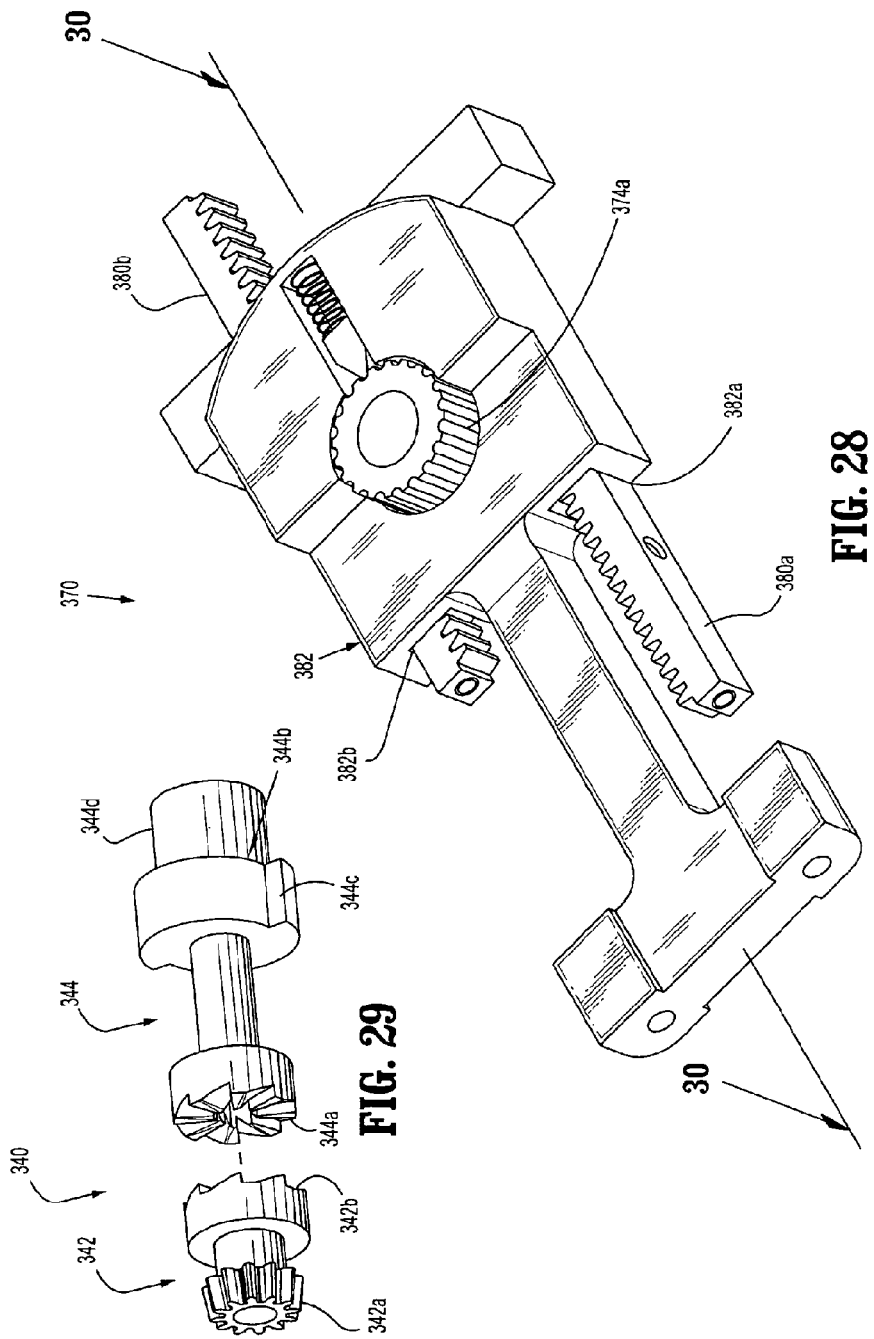

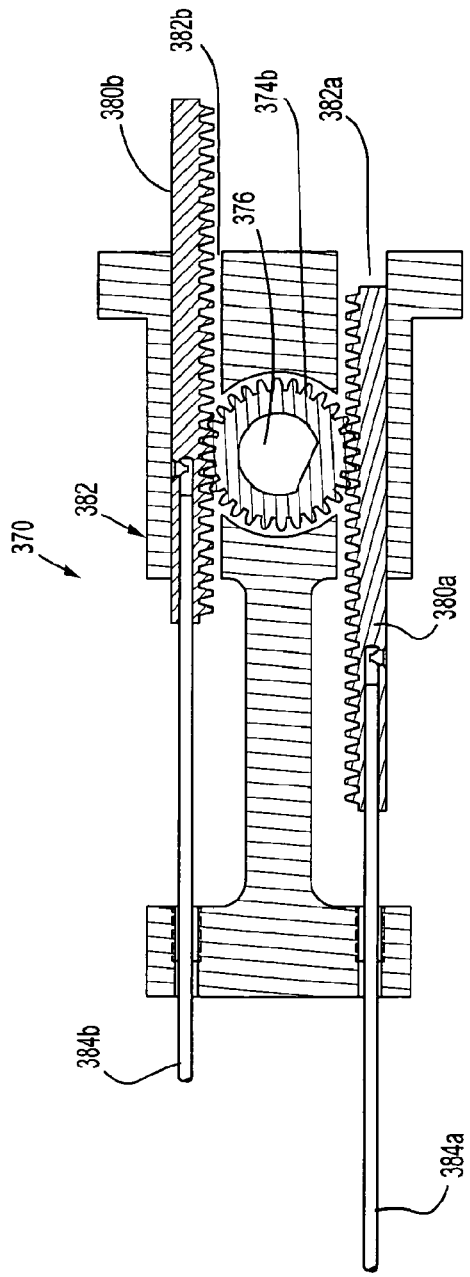
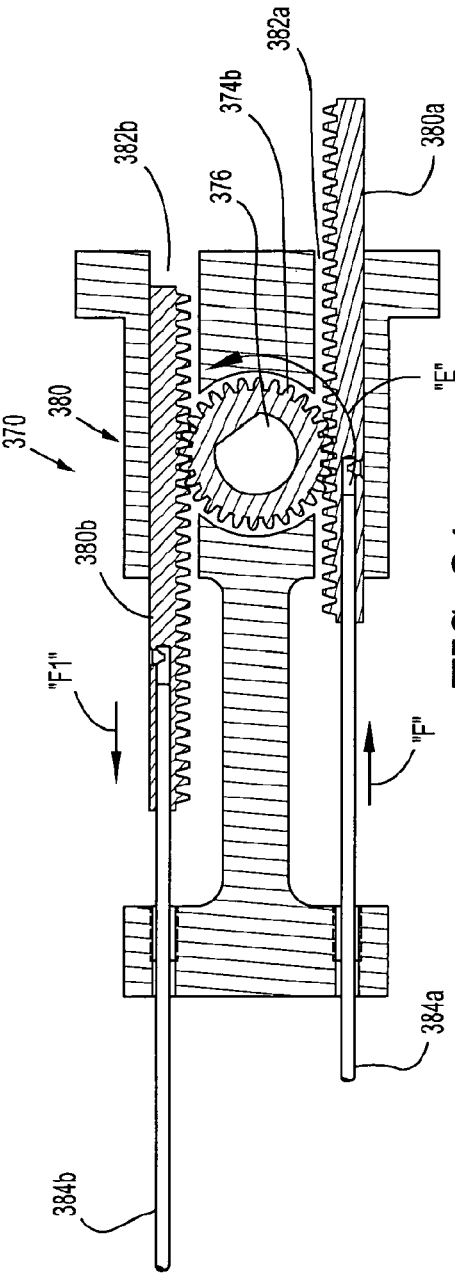
FIG. 30
FIG. 31

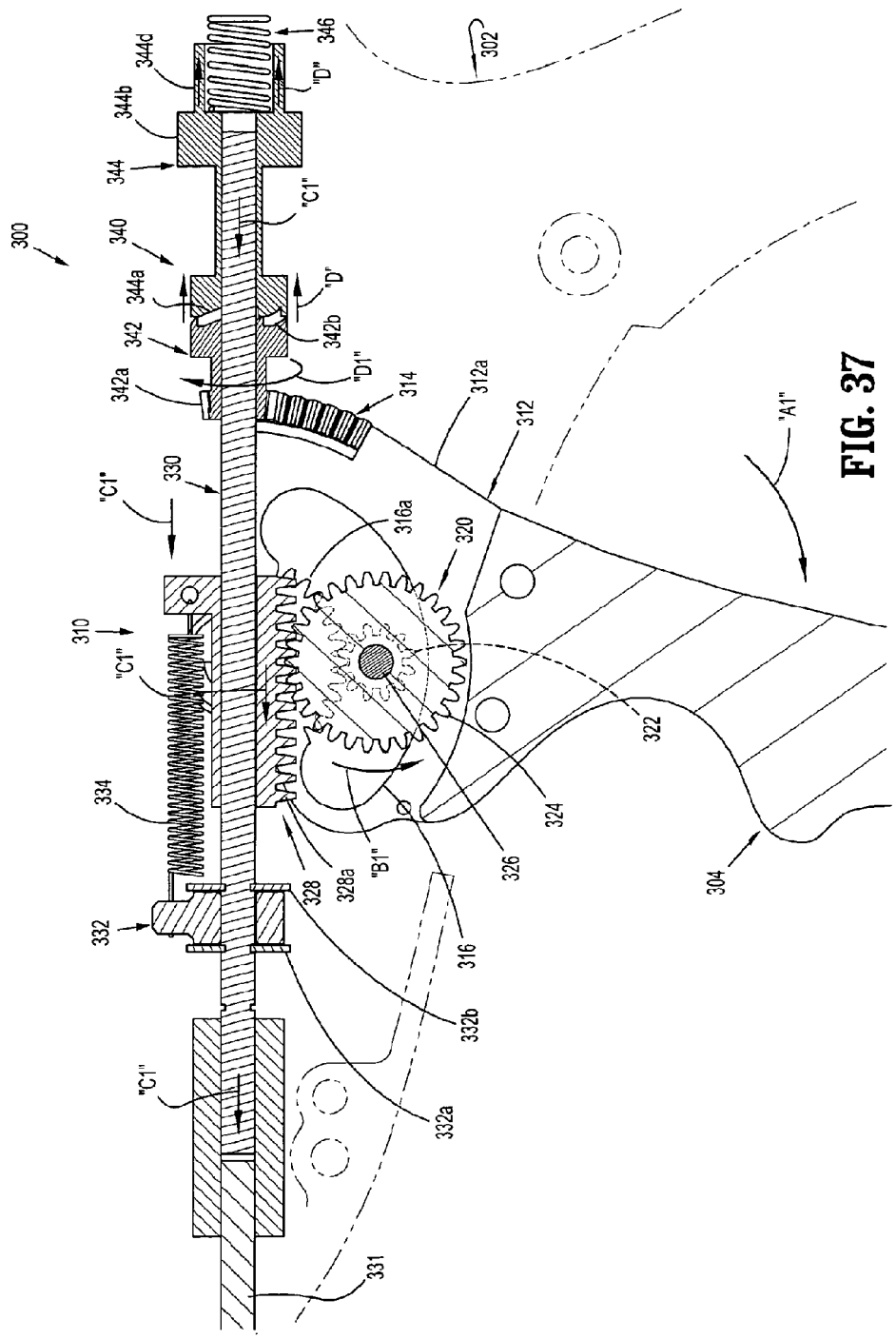

AXIAL STITCHING DEVICE

CROSS-REFERENCE TO RELATED APPLICATIONS

This application is a National Stage Application of PCT/US2007/021482 filed Oct. 4, 2007 under 35 USC §371(a), which claims benefit of and priority to U.S. Provisional Patent Application Ser. No. 60/849,508 filed Oct. 5, 2006; U.S. Provisional Patent Application Ser. No. 60/849,562 filed Oct. 5, 2006; U.S. Provisional Patent Application Ser. No. 60/923,804 filed Apr. 16, 2007 the disclosures of each of the above-identified applications are hereby incorporated by reference in their entirety.

BACKGROUND

1. Technical Field

The present disclosure relates to systems and methods for endoscopic, endoluminal, and/or transluminal suturing and, more particularly, to systems and methods for axial suturing and/or stitching through an access tube or endoscope.

2. Background

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. Also, the reduction in trauma to the abdominal wall and the physiology of the pneumoperitoneum has a positive impact on patients undergoing abdominal operations.

In continuing efforts to reduce the trauma of surgery, interest has recently developed in the possibilities of performing procedures to diagnose and surgically treat a medical condition without any incision in the abdominal wall by using a natural orifice (e.g., the mouth or anus) to access the target tissue. Such procedures are sometimes referred to as endoluminal procedures, transluminal, or natural orifice transluminal endoscopic surgery ("NOTES"). Although many such endoluminal procedures are still being developed, they generally utilize a flexible endoscope instrument or flexible catheter to provide access to the tissue target tissue. Endoluminal procedures have been used to treat conditions within the lumen including for example, treatment of gastroesophageal reflux disease in the esophagus and removal of polyps from the colon. In some instances, physicians have gone beyond the luminal confines of the gastrointestinal tract to perform intra-abdominal procedures. For example, using flexible endoscopic instrumentation, the wall of the stomach can be punctured and an endoscope advanced into the peritoneal cavity to perform various procedures. Using such endoluminal techniques, diagnostic exploration, liver biopsy, cholecystectomy, splenectomy, and tubal ligation have reportedly been performed in animal models. After the intra-abdominal intervention is completed, the endoscopic instrumentation is retracted into the stomach and the puncture closed. Other natural orifices, such as the anus or vagina, may also allow access to the peritoneal cavity.

In many surgical procedures, it is often necessary to suture bodily organs or tissue. Traditionally, suturing was accomplished by hand. Suturing during endoscopic surgery is especially challenging because of the small openings through which the suturing of bodily organs or tissues must be accomplished. Similarly, in endoluminal procedures for example, the site where sutures are to be applied may be deep in a lumen having a tortuous anatomy relatively distant from the access orifice (e.g., mouth or anus).

Many attempts have been made to provide devices to overcome the disadvantages of conventional suturing. Such prior art devices have included staples, clips, clamps or other fasteners. However, none of these above listed devices overcome the disadvantages associated with suturing bodily tissue during endoscopic surgery. Furthermore, even conventional endoscopic stitching devices may not be appropriate for use in some endoluminal procedures because of a rigid shaft that can not easily negotiate the tortuous anatomy of a natural lumen.

Accordingly, there is a need for improvements in suturing devices which overcome the shortcomings and drawbacks of prior art apparatus.

SUMMARY

The present disclosure relates to end effectors, handle assemblies, systems and methods for endoscopic suturing and/or stitching through an access tube or the like.

According to an aspect of the present disclosure, an endoscopic stitching device is provided, including an articulatable neck portion configured and adapted for articulation in at least one direction transverse to a longitudinal axis thereof; an end effector operatively supported on a distal end of the neck assembly; and a suture needle operatively associated with the end effector. The end effector is configured and adapted to selectively engage the suture needle in one of a head assembly and a hub and to axially translate the needle between the head assembly and the hub.

The head assembly may be in juxtaposed relation to the hub. Each of the head assembly and the hub defines a needle retaining recess formed in a tissue contacting surface thereof.

The endoscopic stitching device may further include a translatable needle engaging holding member supported in each of the head assembly and the hub. Each holding member includes an advanced position wherein a feature of the holding member engages the suture needle when the suture needle is in the respective head assembly or hub to thereby secure the suture needle therewith. Each holding member includes a retracted position wherein the feature of the holding member is out of engagement with the suture needle. The endoscopic stitching device includes a cam shaft rotatably supported in the end effector for moving each holding member between the advanced and retracted positions upon a rotation thereof.

The cam shaft may be operatively connected to the head assembly so as to translate the head assembly relative to the hub upon a translation of the cam shaft. A proximal end of the cam shaft may be fixedly secured to an operation cable.

The endoscopic stitching device may further include at least one articulation cable slidably extending through the neck portion and having a distal end fixedly connected to the end effector or a distal end of the neck portion. The articulation cable may be disposed along an axis spaced a distance from a central axis of the neck portion.

According to another aspect of the present disclosure, an endoscopic stitching device is provided including an end effector configured and adapted to perform at least a pair of functions; and a single actuation cable operatively connected to the end effector, wherein the actuation cable is capable of effecting operation of at least the pair of functions. The actuation cable may be capable of effecting a first operation of the pair of functions upon an axial translation thereof; and a second operation of the pair of functions upon a rotation thereof.

The end effector may include a head assembly and a hub in juxtaposed translatable relation relative to one another. Each of the head assembly and the hub may be configured to selectively retain a suture needle.

The actuation cable may be capable of translating the head assembly and the hub relative to one another and of causing retention of the suture needle in a respective one of the head assembly and the hub.

It is contemplated that axial translation of the actuation cable results in translation of the head assembly and the hub relative to one another. It is further contemplated that rotation of the actuation cable results in selective retention of the suture needle in a respective one of the head assembly and the hub.

Each of the head assembly and the hub may define a needle retaining recess formed in a tissue contacting surface thereof.

The endoscopic stitching device may further include a radially translatable needle engaging holding member supported in each of the head assembly and the hub. Each holding member may include an advanced position wherein a feature of the holding member engages the suture needle when the suture needle is in one of the respective head assembly and hub to thereby secure the suture needle therewith; and a retracted position wherein the feature of the holding member is out of engagement with the suture needle.

Rotation of the actuation cable may result in movement of each holding member between the advanced and retracted positions.

The endoscopic stitching device may further include a cam shaft operatively connected to a distal end of the actuation cable such that rotation of the actuation cable results in rotation of the cam shaft wherein the cam shaft is operatively engaged with this needle.

The endoscopic stitching device may still further include at least one articulation cable slidably extending through a neck portion and having a distal end fixedly connected to the end effector. The articulation cable may be disposed along an axis spaced a distance from a central axis of the neck portion.

According to another aspect of the present disclosure, a handle assembly for operating a surgical instrument includes, a housing, a trigger operatively supported on the housing; and at least one actuation cable operatively connected to the trigger and extending from the housing, wherein an actuation of the trigger imparts axial translation and rotation to the actuation cable.

The handle assembly may include at least one articulation cable operable from the housing. Each articulation cable includes a distal end operatively connectable with an end effector and a proximal end operatively connected to at least one of a control element, such as, for example, a slider, dial, lever, or the like, supported on the housing. In operation, movement of the control element results in movement of the at least one articulation cable, wherein movement of the at least one articulation cable in a first direction causes an articulation of the end effector and movement of the at least one articulation cable in a second direction results in articulation of the end effector in a second direction.

The control element may include a trigger plate defining a gear segment operatively engaging at least one gear operatively connected to an actuation shaft, wherein movement of the control element results in at least rotation of the actuation shaft. The control element may be operatively connected to the actuation shaft such that movement of the control element results in axial translation of the actuation shaft.

According to a further aspect of the present disclosure, an axial stitching device is provided and includes a handle assembly for operating the axial stitching device. The handle assembly includes a housing; a trigger operatively supported on the housing; and at least one actuation cable operatively connected to the trigger and extending from the housing, wherein an actuation of the trigger imparts axial translation and rotation to the actuation cable. The axial stitching device further includes an articulatable neck portion supported on the handle assembly, wherein the articulatable neck portion is configured and adapted for articulation in at least one direction transverse to a longitudinal axis thereof; an end effector operatively supported on a distal end of the neck assembly; and a suture needle operatively associated with the end effector. The end effector is configured and adapted to selectively engage the suture needle in one of a head assembly and a hub upon rotation of the actuation cable and to axially translate the needle between the head assembly and the hub upon axial translation of the actuation cable.

The handle assembly may include at least one articulation cable operable from the housing. Each articulation cable may include a distal end operatively connectable with the end effector and a proximal end operatively connected to at least one of a control element, a slider, a dial, and a lever supported on the housing.

In use, movement of the control element may result in movement of the at least one articulation cable. Additionally, in use, movement of the at least one articulation cable in a first direction may cause an articulation of the end effector in a first direction and movement of the at least one articulation cable in a second direction may result in articulation of the end effector in a second direction.

The control element may include a trigger plate defining a gear segment operatively engaging at least one gear operatively connected to an actuation shaft. In use, movement of the control element may result in at least rotation of the actuation shaft. The control element may be operatively connected to the actuation shaft such that movement of the control element results in axial translation of the actuation shaft.

The head assembly may be in juxtaposed relation to the hub.

Each of the head assembly and the hub may define a needle retaining recess formed in a tissue contacting surface thereof.

The axial stitching device may further include a radially translatable needle engaging holding pin supported in each of the head assembly and the hub. Each holding pin may include an advanced position wherein an end of the holding pin engages the suture needle when the suture needle is in one of the respective head assembly and hub to thereby secure the suture needle therewith. Each holding pin may include a retracted position wherein the end of the holding pin is out of engagement with the suture needle.

The axial stitching device may further include a cam shaft rotatably supported in the end effector for moving each holding pin between the advanced and retracted positions upon a rotation thereof. The cam shaft may be operatively connected to the head assembly so as to translate the head assembly relative to the hub upon a translation of the cam shaft. A proximal end of the cam shaft may be fixedly secured to an operation cable.

The suture needle may include a length of barbed suture extending therefrom.

DETAILED DESCRIPTION OF THE DRAWINGS

The foregoing objects, features and advantages of the disclosure will become more apparent from a reading of the following description in connection with the accompanying drawings, in which:

FIG. 3 is a perspective, longitudinal cross-sectional view of the distal end of the stitching device of FIGS. 1 and 2;

FIG. 4 is a rear perspective view of the distal end of the stitching device of FIGS. 1-3;

FIG. 5 is a perspective view of a distal end of a cam shaft of the distal end of the stitching device of FIGS. 1-4;

FIG. 6 is a perspective view of a suture needle according to an embodiment of the present disclosure;

FIG. 7 is a side-elevational view of the longitudinal cross-section of the distal end of the stitching device of FIG. 3;

FIG. 8 is an enlarged view of the indicated area of detail of FIG. 7;

FIG. 19 is a cross-sectional view of the handle assembly of FIGS. 15-18, as taken through 19-19 of FIG. 17;

FIG. 20 is a perspective view of drive assembly of the handle assembly of FIGS. 15-19;

FIG. 21 is a perspective view of a slide actuator of the handle assembly of FIGS. 15-19;

FIG. 28 is a perspective view of an articulation control mechanism of the handle assembly of FIGS. 24-27;

FIG. 29 is a perspective view of a slip-clutch of the handle assembly of FIGS. 24-27;

FIG. 30 is a cross-sectional view of the articulation control mechanism of FIG. 28 as taken through 30-30 of FIG. 28;

FIG. 31 is a cross-sectional view of the articulating control mechanism of FIG. 28, as taken through 30-30 of FIG. 28, illustrating the operation thereof;

FIG. 37 is a side elevational view of the drive mechanism of FIG. 33, illustrating the drive mechanism and the trigger of the handle assembly in a fourth position;

DETAILED DESCRIPTION OF EMBODIMENTS

Figure 1:
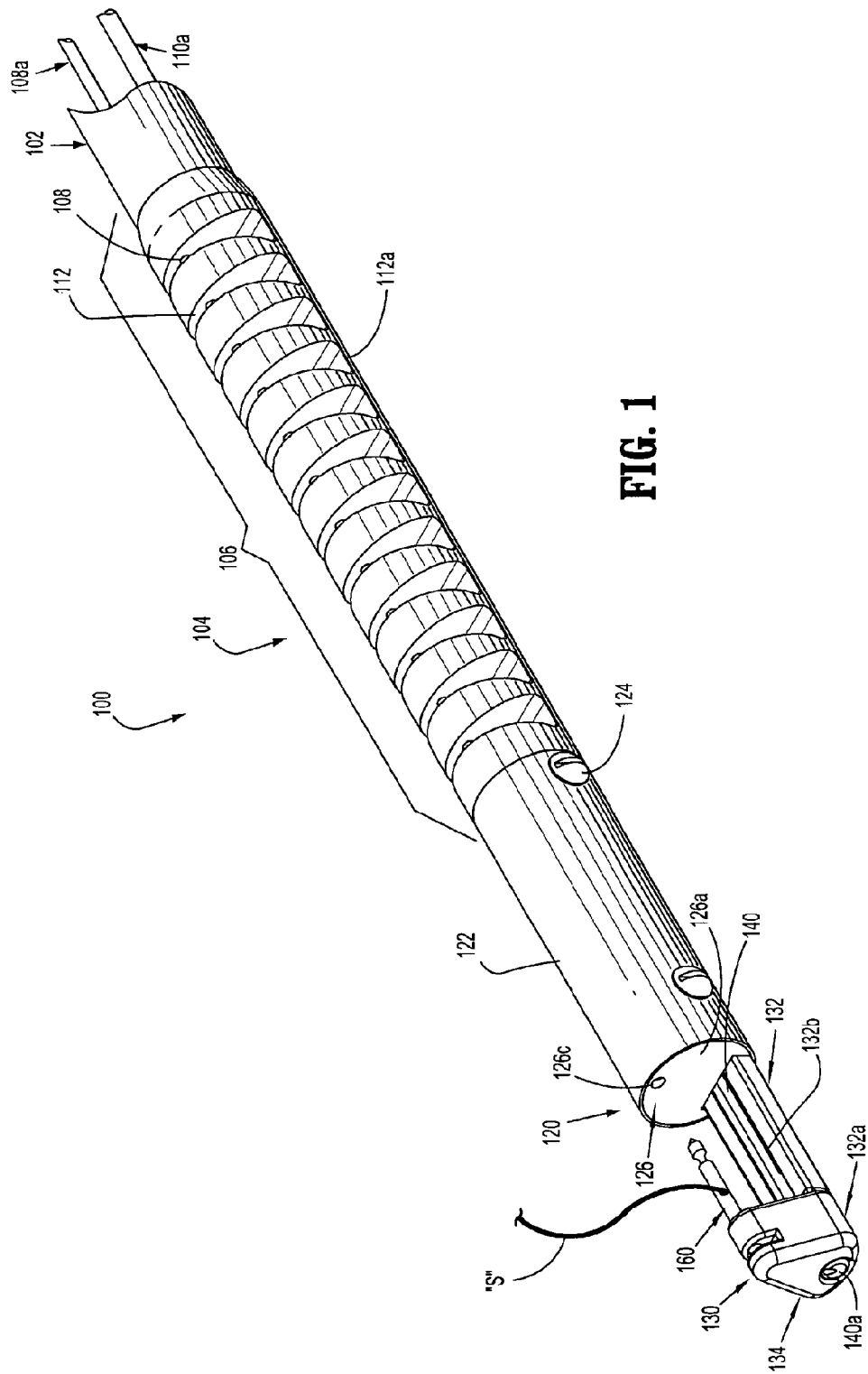
FIG. 1 is a perspective view of a distal end of a stitching device according to an embodiment of the present disclosure.
Figure 2:
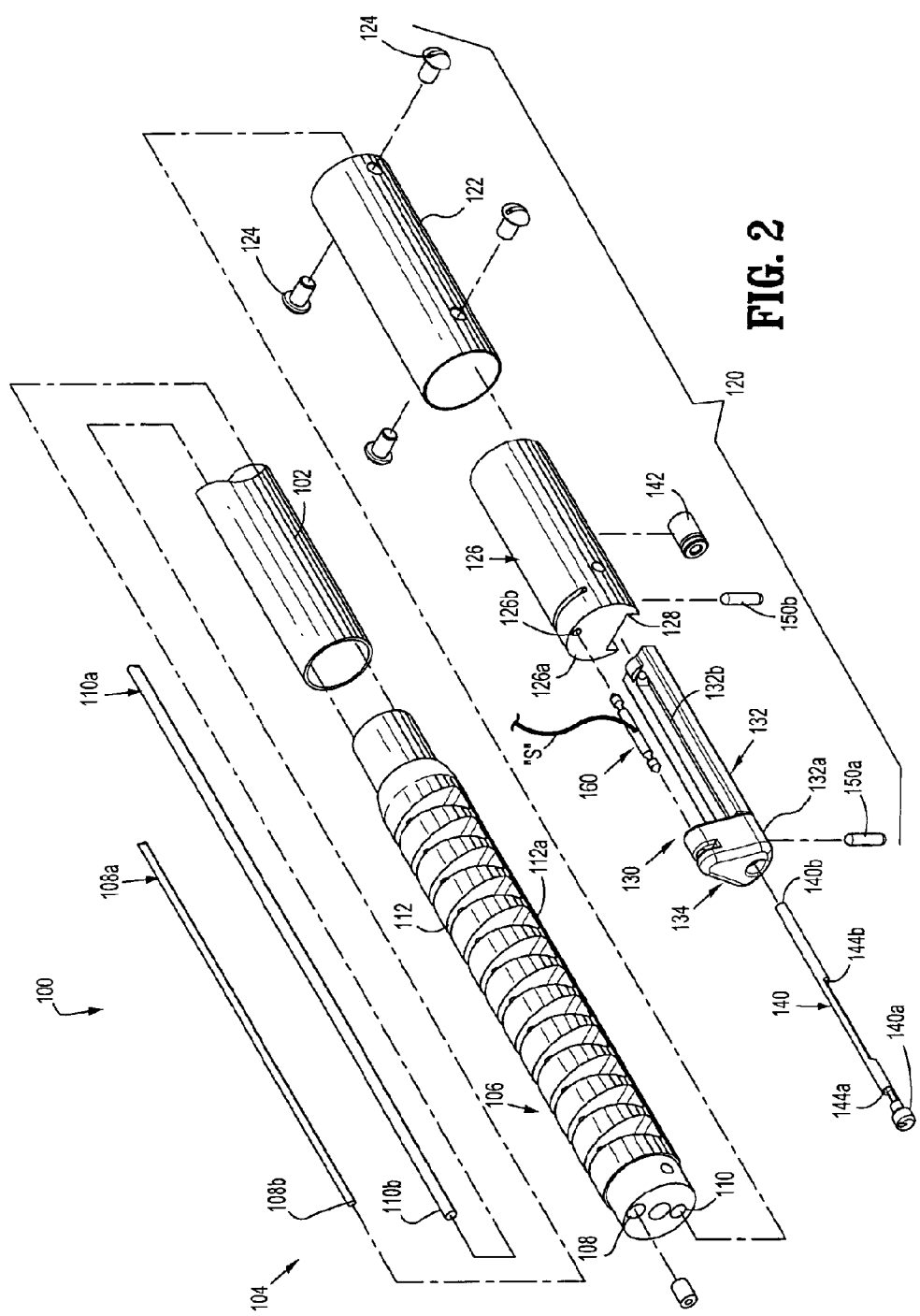
FIG. 2 is an exploded perspective view of the distal end of the stitching device of FIG. 1.

In the drawings and in the description which follow, the term "proximal", as is traditional, will refer to the end of the device which is closest to the operator, while the term "distal" will refer to the end of the device which is furthest from the operator.

The present disclosure relates to devices, systems and methods for endoscopic and/or endoluminal suturing. In one embodiment, for example, such a device comprises a handle, handle assembly or other suitable actuating mechanism (e.g., robot, etc.) connected to a proximal end of a flexible, elongated body portion. A neck portion operatively supported on a distal end of the flexible, elongated body portion allows an end effector, operatively supported at a distal end of the neck portion, to articulate in response to actuation of an articulation cable. The end effector includes a suture needle and a mechanism to pass the needle back and forth along a longitudinal axis of the end effector. The device is adapted to be placed in a lumen of a flexible endoscope and then inserted into a natural orifice of a patient and transited endoluminally through the anatomy of the natural lumen to a treatment site.

Referring now in specific detail to the drawings, in which like reference numbers identify similar or identical elements, FIGS. 1-8 illustrate one embodiment of a stitching device, shown generally at 100. Stitching device 100 is adapted to be particularly useful in endoscopic, laparoscopic, or endoluminal procedures wherein an endoscopic portion of the stitching device 100 is insertable into an operative site, via a trocar, flexible endoscope, flexible catheter, cannula assembly, or the like (not shown).

As seen in FIGS. 1-8, stitching device 100 includes a handle assembly (not shown) and an elongate tubular body portion 102 extending distally from the handle assembly and defining a longitudinal axis and a lumen therethrough. In one embodiment, tubular body portion 102 is preferably flexible, for example, to allow the device to be inserted through a lumen of a flexible endoscope of other similar device. Such a flexible tubular body portion 102, may be rotationally rigid, by for example incorporating a flexible woven steel tube into the tubular body portion 102. In an alternative embodiment, the tubular body portion 102 is rigid or substantially rigid. A tool assembly 104 is operatively associated with or supported on a distal end of elongate body portion 102 and is remotely operable by the handle assembly.

Tool assembly 104 includes a neck portion 106 extending axially from elongate tubular body portion 102. Neck portion 106 defines at least a first and a second lumen 108, 110, respectively extending therethrough. Neck portion 106 further defines at least one radially oriented groove 112 formed therein and extending beyond a longitudinal central axis thereof. In an embodiment, neck portion 106 includes a plurality of transversely oriented grooves 112 formed therein, with each groove 112 extending beyond the longitudinal central axis thereof. A spine 112a extends across and between each groove 112. In an embodiment, grooves 112 may be configured so as to enable either bi-directional of four-way articulation of tool assembly 104.

As seen in FIGS. 3, 7 and 8, first lumen 108 extends through neck portion 106 at a location proximate open ends of grooves 112. An articulation cable or wire 108a extends through first lumen 108 and includes a distal end 108b anchored or otherwise suitably secured to a distal location, preferably at a point distal of distal-most groove 112. In this manner, as will be discussed in greater detail below with regard to FIG. 14, in operation, as articulation cable 108a is drawn in a proximal direction (as indicated by arrow "D"), tool assembly 104 is caused to bend, deflect and/or otherwise articulate relative to the longitudinal axis, along a neutral axis thereof. Additionally, as seen in FIGS. 3, 7 and 8, second lumen 110 extends through spine 112a of neck portion 106. An operation cable 110a extends through second lumen 110 and includes a distal end 110b extending into end effector 120 of tool assembly 104.

In an alternative embodiment, articulation cable 108a and operation cable 110a extend through a single lumen. In such embodiment, the cables may, for example, be coaxial with the operation cable 110a formed as a tube with a lumen and the articulation cable 108a extending through the lumen of the operation cable 110a. Alternatively, articulation cable 108a may be formed as a tube with a lumen and the operation cable 110a extending through the lumen of the articulation cable 108a.

Tool assembly 104 includes an end effector 120 operatively supported on a distal or free end of neck portion 106. End effector 120 includes a support tube 122 secured to distal end of neck portion 106 by suitable fastening members 124, such as, for example, screws or the like. End effector 120 includes a hub 126 disposed within support tube 122. A longitudinal channel 128 is defined either in hub 126 or between hub 126 and support tube 122. Longitudinal channel 128 is operatively aligned with second lumen 110 of neck portion 106.

End effector 120 includes a head assembly 130 slidably supported on hub 126 and/or between hub 126 and support tube 122. Head assembly 130 includes an arm 132 slidably disposed within channel 128 and extending distally therefrom, and a head 134 supported on a distal end 132a of arm 132. Arm 132 defines a longitudinal groove 132b formed in a surface thereof and axially aligned with longitudinal channel 128 of hub 126 and second lumen 110 of neck portion 104.

End effector 120 includes a cam shaft or crank 140 rotatably disposed within groove 132b of arm 132. It is contemplated that either a cam shaft or a crank, as used herein, may be able to impart a pushing and/or a pulling force. As seen in FIGS. 2, 3, 5 and 8, cam shaft 140 is in elongate cylindrical body having a distal end 140a rotatably supported in head 134 of head assembly 130 and a proximal end 140b fixedly coupled to or otherwise suitably operatively secured to distal end 110b of operation cable 110a. A coupler 142 may be used to join proximal end 140b of cam shaft 140 to distal end 110b of operation cable 110. Coupler 142 also functions to maintain cam shaft 140 in groove 132b of arm 132.

Cam shaft includes a first or distal lobe 144a in the form of a relief or the like, and a second or proximal lobe 144b in the form of a relief or the like. Second lobe 144b is elongate and is oriented or disposed on a side of cam shaft 140 opposite first lobe 144a.

End effector 120 further includes a first holding pin or member 150a slidably disposed within a lumen 134a of head 134, and a second holding pin or member 150b slidably disposed within a lumen 126b of hub 126. Lumens 134a and 126b are configured and shaped so that respective holding pins 150a, 150b selectively engage an outer surface of cam shaft 140 and, preferably, respective lobes 144a, 144b of cam shaft 140. Lumen 134a of head 134 opens, at a first end, to groove 132b of arm 132, and at a second end to an axial needle retaining recess 134b. Lumen 126b of hub 126 opens, at a first end, to channel 128 and at a second end to an axial needle retaining recess 126b. Needle retaining recess 134b of head 134 is in juxtaposed alignment with needle retaining recess 126c of hub 126.

In operation, as will described in greater detail below, as cam shaft 140 is rotated about a longitudinal axis thereof, holding pins 150a, 150b will rise and fall, within respective lumens 134a, 126b, as respective lobes 144a, 144b of cam shaft 140 come into and out of operative association with respective holding pin 150a, 150b. Rotation of operation cable 110a imparts rotation to cam shaft 140, as will be described in greater detail below.

Stitching device 100 further includes a suture needle 160 selectively movable from needle retaining recess 134b of head 134 and needle retaining recess 126c of hub 126. As seen in FIGS. 1-4 and 6-8, suture needle 160 includes a body portion 162 having a sharpened first tip 162a and a sharpened second tip 162b. Suture needle 160 further includes a first annular recess 164a formed in body portion at a location proximate first tip 162a and a second annular recess 164b formed in body portion at a location proximate second tip 162b. A suture "S" is secured to body portion 162 at a location between annular recesses 164a, 164b.

In operation, as will be described in greater detail below, first annular recess 164a is configured and adapted to selectively engage, mate and/or receive first holding pin 150a, and second annular recess 164b is configured and adapted to selectively engage, mate and/or receive second holding pin 150b.

Figure 9:
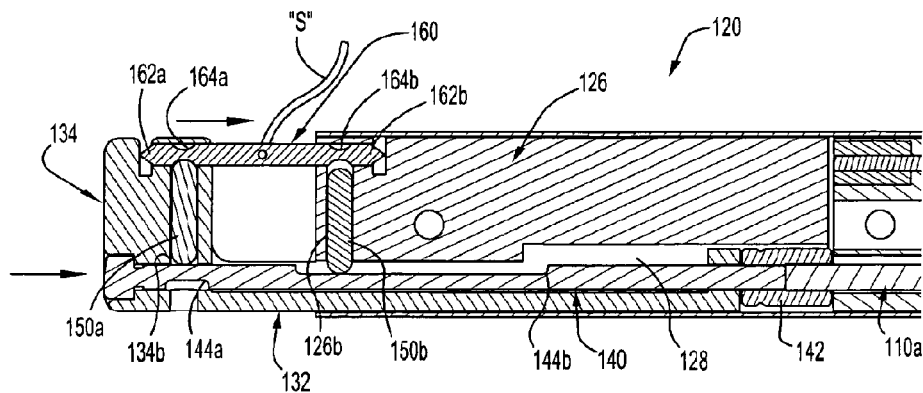
FIGS. 9-13 are each side-elevational, cross-sectional views of the distal end of the stitching device of FIGS. 1-4, illustrating a method of operation thereof.

Turning now to FIGS. 9-13, a method of operating stitching device 100 is provided. Initially, as seen in FIG. 9, head 134 of head assembly 130 is approximated toward hub 126, to grasp one or more layers of tissue, to penetrate needle 160 through at least one layer of tissue (not shown), and to introduce second tip 162b of needle 160 into needle retaining recesses 126c of hub 126. Needle 160 is held in position in needle retaining recess 134b of head 134 by first holding pin 150a which is in a raised position in engagement with first annular recess 164a of needle 160.

First holding pin 150a is in the raised position as a result of the angular orientation of cam shaft 140. As seen in FIG. 9, first lobe 144a of cam shaft 140 is out of angular registration with lumen 134a of head 134 and thus first holding pin 150a is held in the raised position by the surface of cam shaft 140.

Head 134 of head assembly 130 is approximated toward hub 126 by withdrawing on operation cable 110a which in turn pulls on cam shaft 140 and slidably draws arm 132 of head assembly 130 through channel 128 of hub 126. With head 134 in the approximated position and first holding pin 150a held in the raised position by cam shaft 140, second holding pin 150b is permitted to fall freely into second lobe 144b of cam shaft 140, as a location proximate a distal end thereof.

Figure 10:
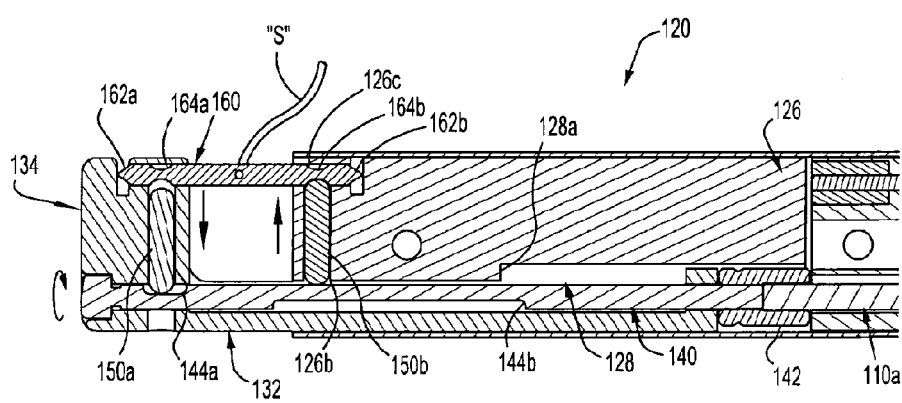

As seen in FIG. 10, with second tip 162b in needle retaining recess 126c of cam shaft 140 is rotated about a longitudinal axis thereof to disengage first holding pin 150a from needle 160 and engage second holding pin 150b with needle 160. In particular, as cam shaft 140 is rotated, first lobe 144a thereof is rotated to operative registration with lumen 134b of head 134. As such, as tension is applied to needle 160, annular recesses 164a, 164b of needle 160 act on respective first or second holding pins 150a, 150b in order to move or urge holding pins 150a, 150b out of engagement with needle 160. Concomitantly therewith, as cam shaft 140 is rotated, second lobe 144b of cam shaft is rotated out of registration with lumen 126b of hub 126 thus forcing second holding pin 150b therethrough and into operative engagement with second annular recess 164b of needle 160. As such, needle 160 is held in position in needle retaining recess 126c of hub 126.

Figure 11:
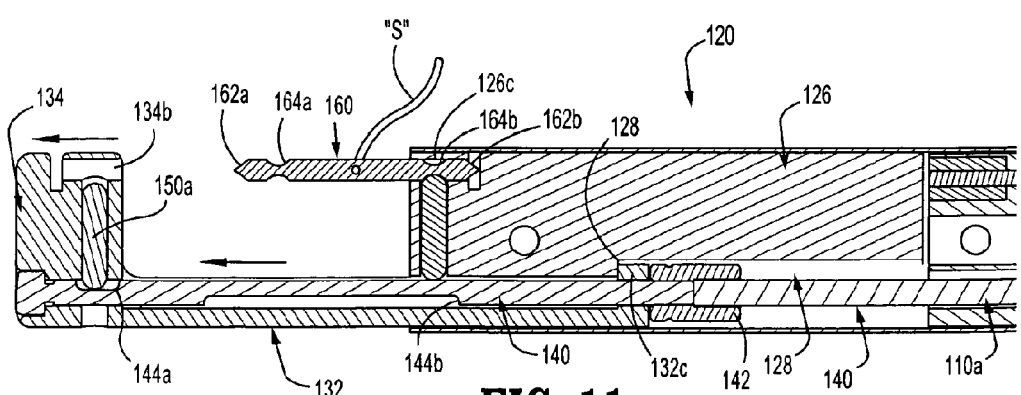
Figure 12:
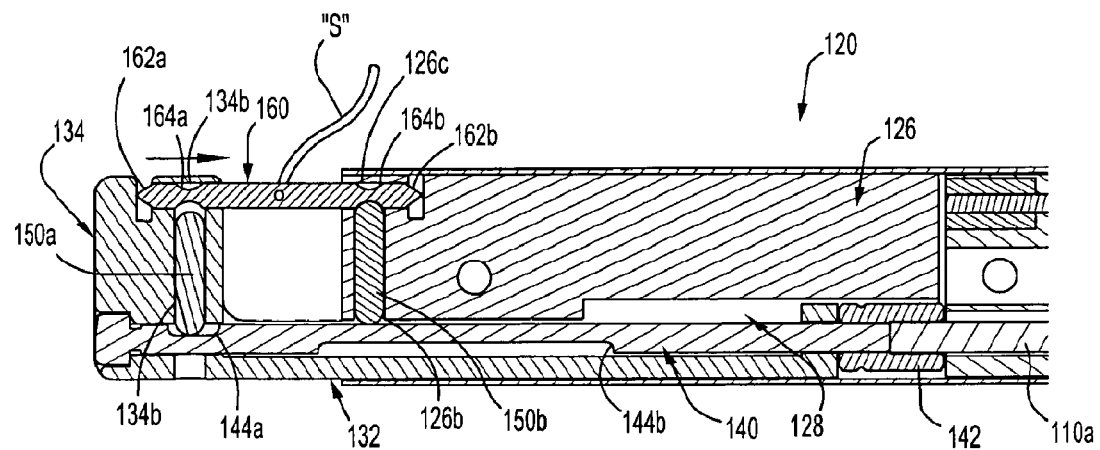

Referring now to FIG. 11, with needle 160 secured and/or otherwise held in needle retaining recess 126c of hub 126, head 134 of head assembly 130 is moved away from hub 126 to disengage first tip 162a of needle 160 from needle retaining recess 134b of head 134. Head 134 is moved away from hub 126 by advancing operation cable 110a in a proximal direction relative to hub 126. In so doing, arm 132 may be advanced distally until a shoulder 132c of arm 132, disposed within channel 128 abuts against a shoulder 128a of channel 128. When arm 132 is in a fully advanced position, a proximal end of second lobe 144b of cam shaft 140 is located proximate second holding needle 150b and/or lumen 126b of hub 126.

With needle 160 so positioned, end effector 120 is repositioned relative to the target tissue and head 134 of head assembly 130 re-approximated toward hub 126. As discussed above and as seen in FIG. 12, head 134 is reapproximated toward hub 126 by withdrawing on operation cable 110a which in turn pulls on cam shaft 140 and slidably draws arm 132 of head assembly 130 through channel 128 of hub 126.

Figure 13:
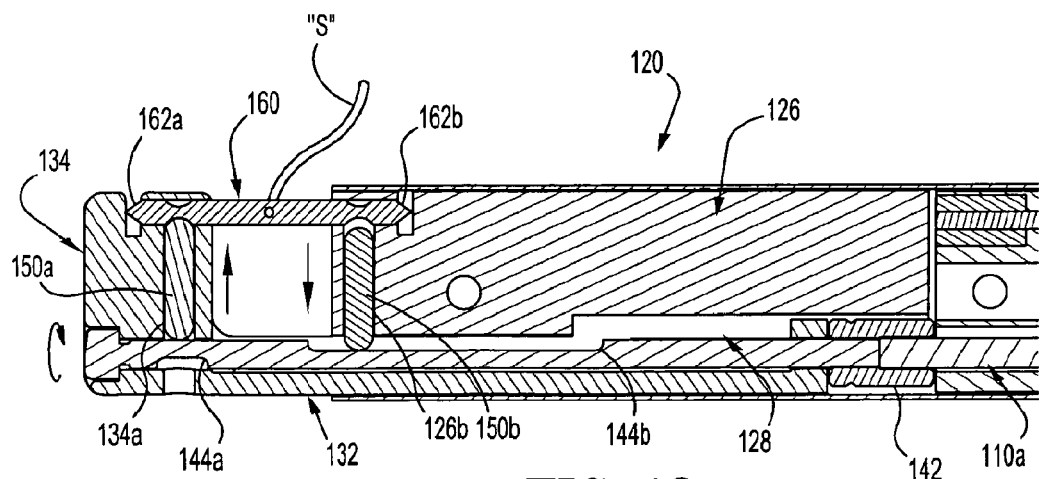

As seen in FIG. 13, with head 134 in the reapproximated position, first holding pin 150a is re-raised into operative engagement with first annular recess 164a of needle 160 by rotating cam shaft 140 to rotate first lobe 144b out of registration with lumen 134b of head 134 and pushing first holding pin 150a up, therethrough, into engagement with first annular recess 164a of needle 160. As such, as tension is applied to needle 160, annular recess 164a of needle 160 acts on respective first holding pin 150a in order to move or urge second holding pin 150a out of engagement with needle 160.

Figure 14:
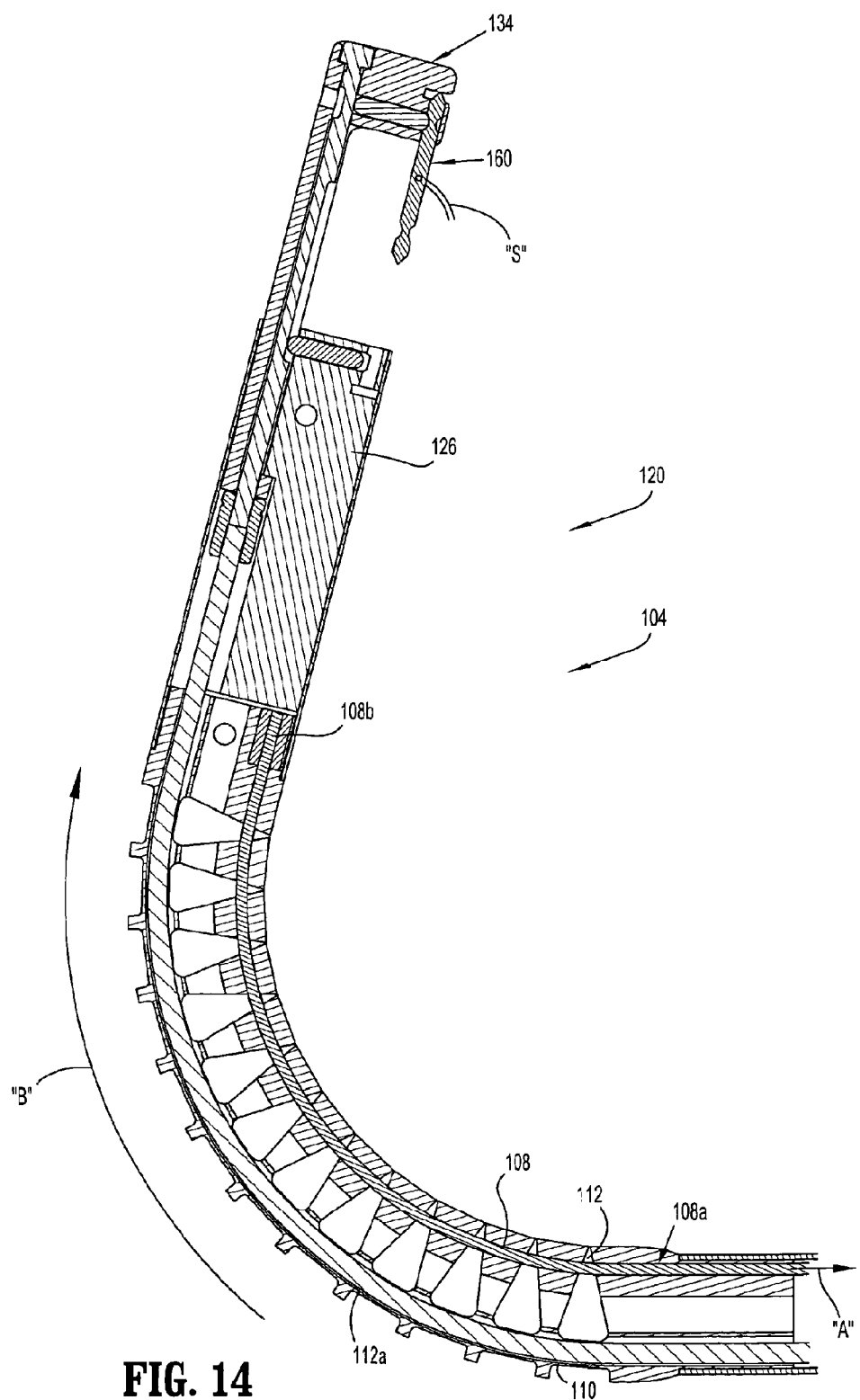
FIG. 14 is a side-elevational view of the distal end of the stitching device of FIGS. 1-4, illustrating an articulation thereof.

With reference to FIG. 14, end effector 120 may be articulated at neck portion 106, as indicated by arrow "B", by withdrawing on articulation cable 108a in a proximal direction (as indicated by arrow "A"). Since distal end 108b of actuation cable 108a is secured to either neck portion 106, at a location distal of grooves 112, or secured to hub 126, withdrawal of actuation cable 108a causes grooves to constrict about spine 112a and end effector 120 to bend. In an alternative embodiment (not shown), end effector 120 may be articulated at neck portion 106 by pushing on articulation cable 108a in a distal direction.

It is envisioned and within the scope of the present disclosure for actuation cable 108a and operation cable 110a to be constructed from a suitable material capable of imparting and/or transmitting axial tension and/or compression forces and/or rotational torsional forces. Such as suitable material includes, and is not limited to stainless steel, nickel-titanium alloys, etc. For example, operation cable 110a may be fabricated from a spiral wrapped flexible cable and actuation cable 108a may be fabricated from a twisted, stranded "wire rope".

Operation cable 110a is capable of performing two functions as described in detail above, namely, movement of cam shaft 140 in an axial direction both distally and proximally to approximate and distance head 134 and hub 126 relative to one another, and rotation of cam shaft 140 about a longitudinal axis thereof to selectively actuate first and second holding pins 150a, 150b into and out of operative engagement with needle 160.

One exemplary method of using stitching device 100 includes the use of stitching device 100 to close opening, punctures, etc. formed in a wall of a corporal lumen (i.e., esophagus, intestine, etc.) or corporal organ (e.g., stomach) following a surgical procedure. By way of example only, for a laparoscopic procedure, a scope may be inserted into a patients stomach, through a patients mouth and esophagus. At least one opening or puncture may be created in the wall of the stomach or other gastric wall and the surgical procedure performed in the abdominal cavity using suitable endoscopic and/or endoluminal surgical devices. Once the surgical procedure has been completed, for example, in the abdominal cavity, either prior to or following the removal of the scope from the patient, stitching device 100 may be used, as described above, to close the opening or puncture created in the wall of the stomach or other gastric wall.

Various handles and/or handle assemblies may be operatively connected or otherwise associated with stitching device 100 in order to effect operation and movement of the various components thereof. Exemplary handles and/or handle assemblies for use with stitching device 100 are disclosed in U.S. Provisional Application Ser. No. 60/849,560, filed on Oct. 5, 2006, entitled "FLEXIBLE ARTICULATED ENDOSCOPIC INSTRUMENT"; the entire disclosures of which is incorporated herein by reference.

The various handle and/or assemblies for manipulating and/or operating endoscopic and endoluminal surgical suturing and/or stitching devices instruments include an actuation component (e.g., actuation cable) for producing and/or imparting a combination of axial motion and rotational motion. In this manner, the handle assembly is thus capable of producing a programmed function of axial motion (i.e., push and pull) and rotational motion.

Figure 16:
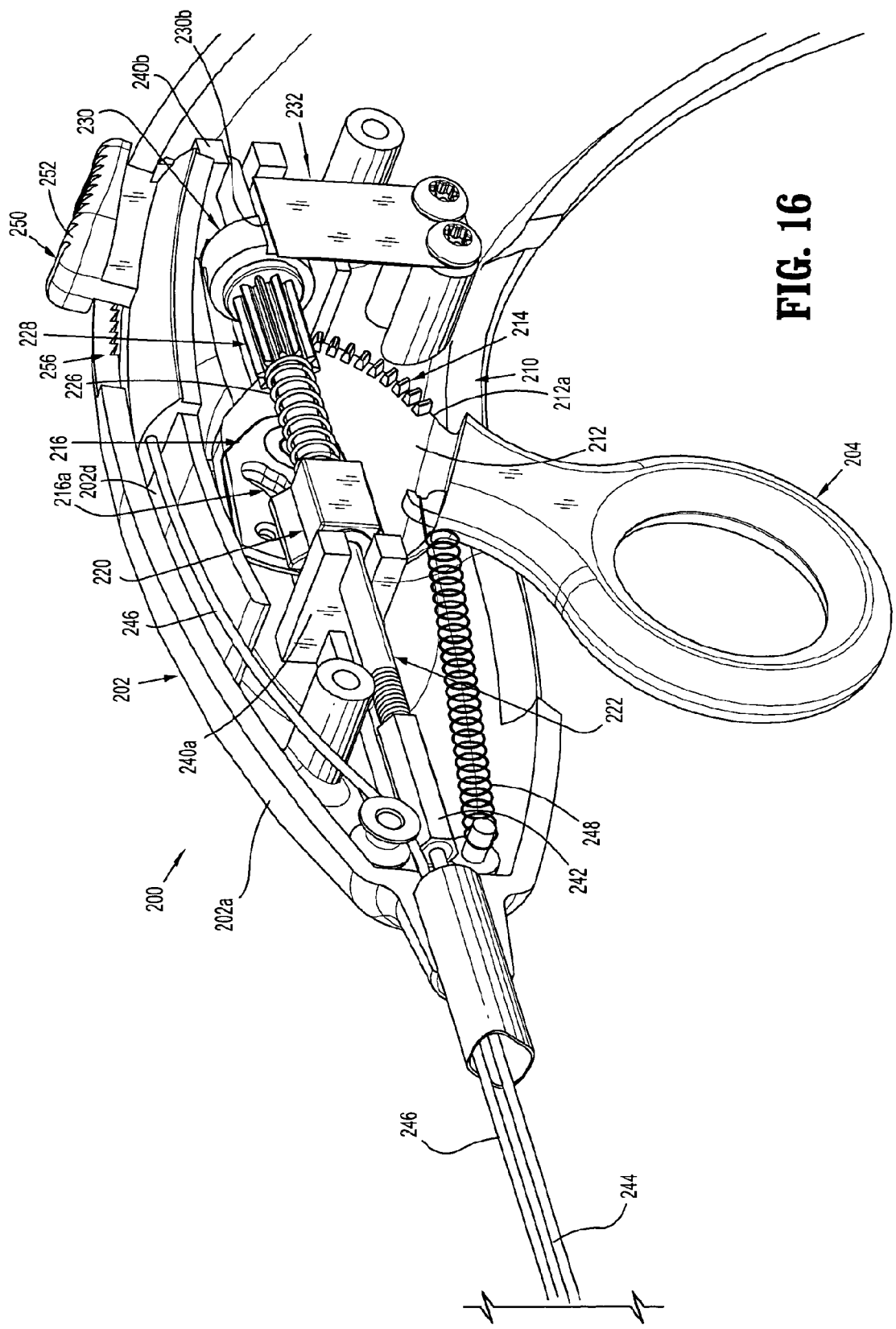
FIG. 16 is a perspective view of the handle assembly of FIG. 15, with a half-section of the housing removed therefrom.
Figure 17:
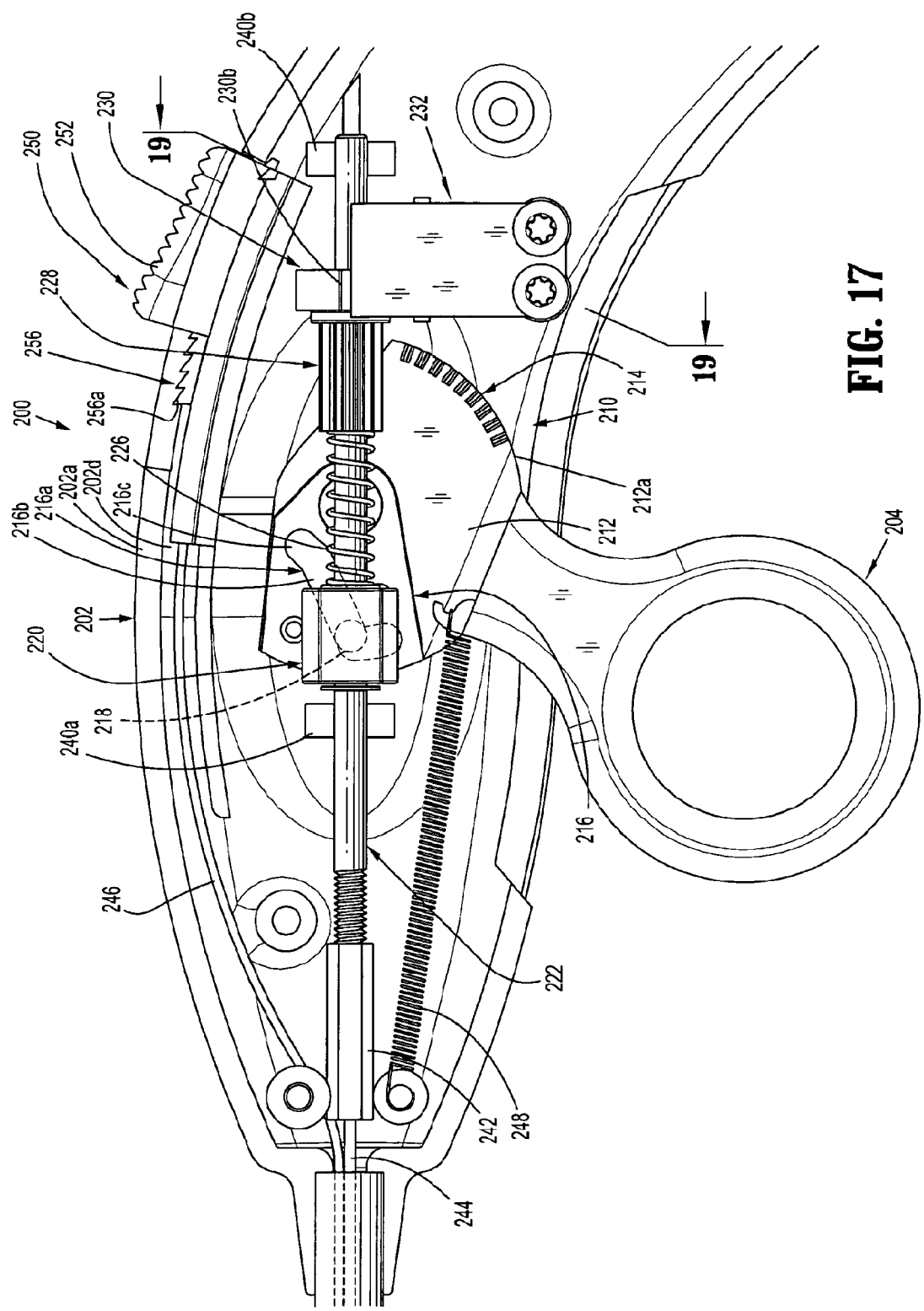
FIG. 17 is a side elevational view of the handle assembly of FIG. 16, illustrating a trigger of the handle assembly in a first position.
Figure 18:
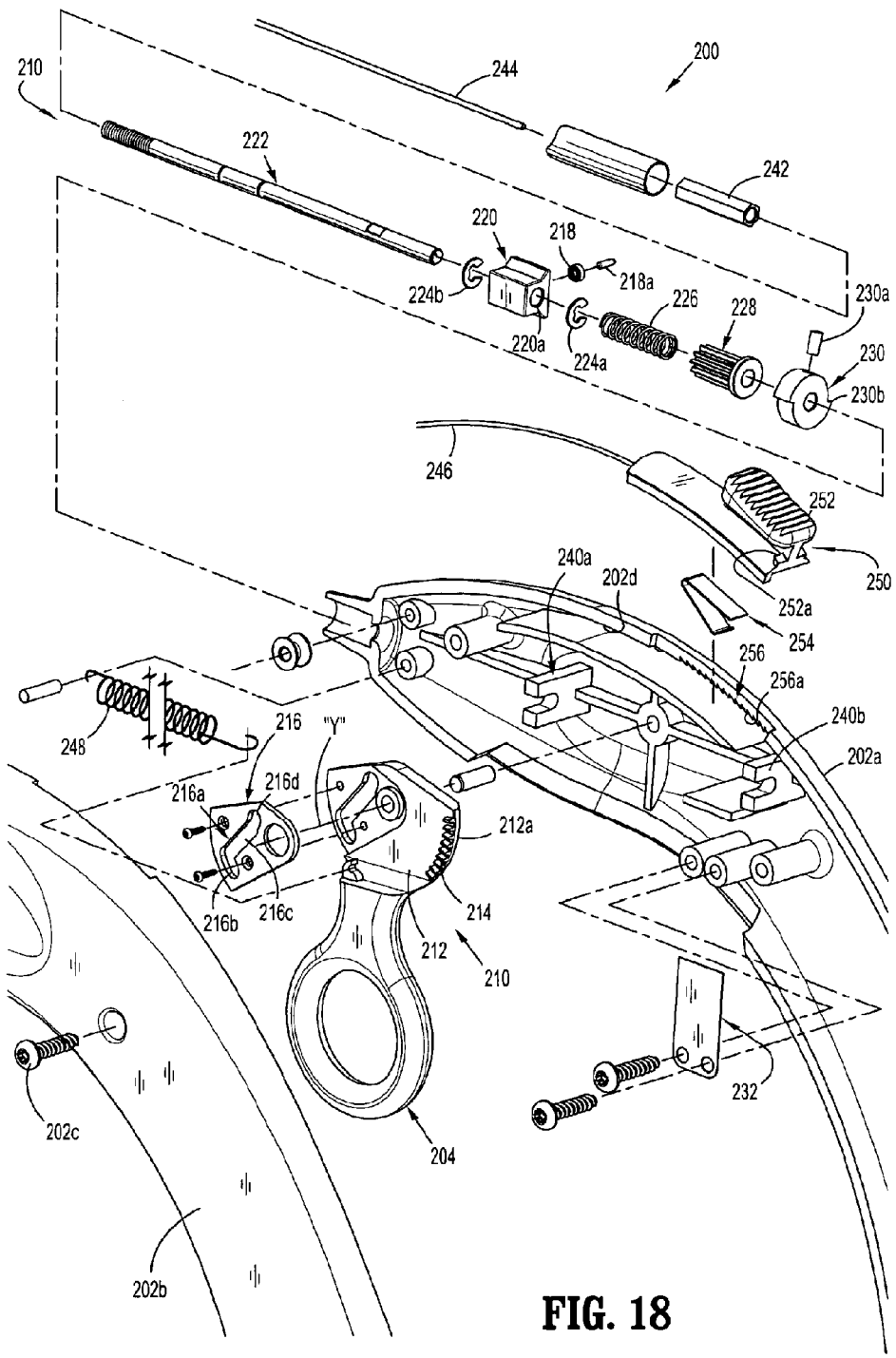
FIG. 18 is an exploded perspective view of the handle assembly of FIGS. 16 and 17.

Referring now to FIGS. 15-23, a handle assembly, in accordance with an embodiment of the present disclosure, for operating, manipulating and/or controlling an endoscopic device, such as stitching device 100, is generally designated as 200. Handle assembly 200 includes a housing 202 having a right-half section 202*a* and a left-half section 202*b* joinable to one another by suitable fastening elements 202*c*, such as screws 202*c*, as shown in FIG. 18.

Figure 15:
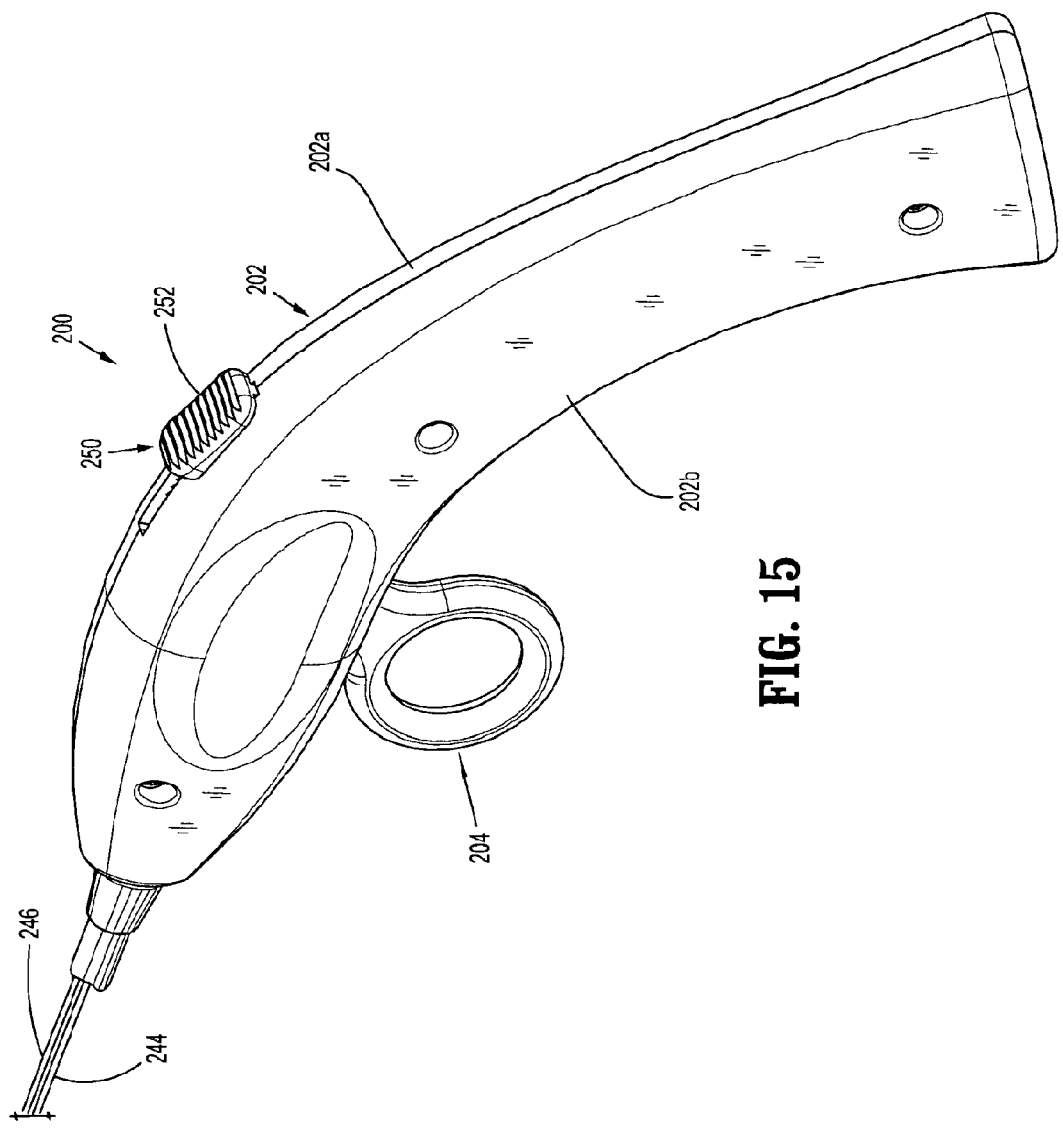
FIG. 15 is a perspective view of a handle assembly, according to an embodiment of the present disclosure, for use with the distal end of the stitching device of FIGS. 1-14.
Figure 22:
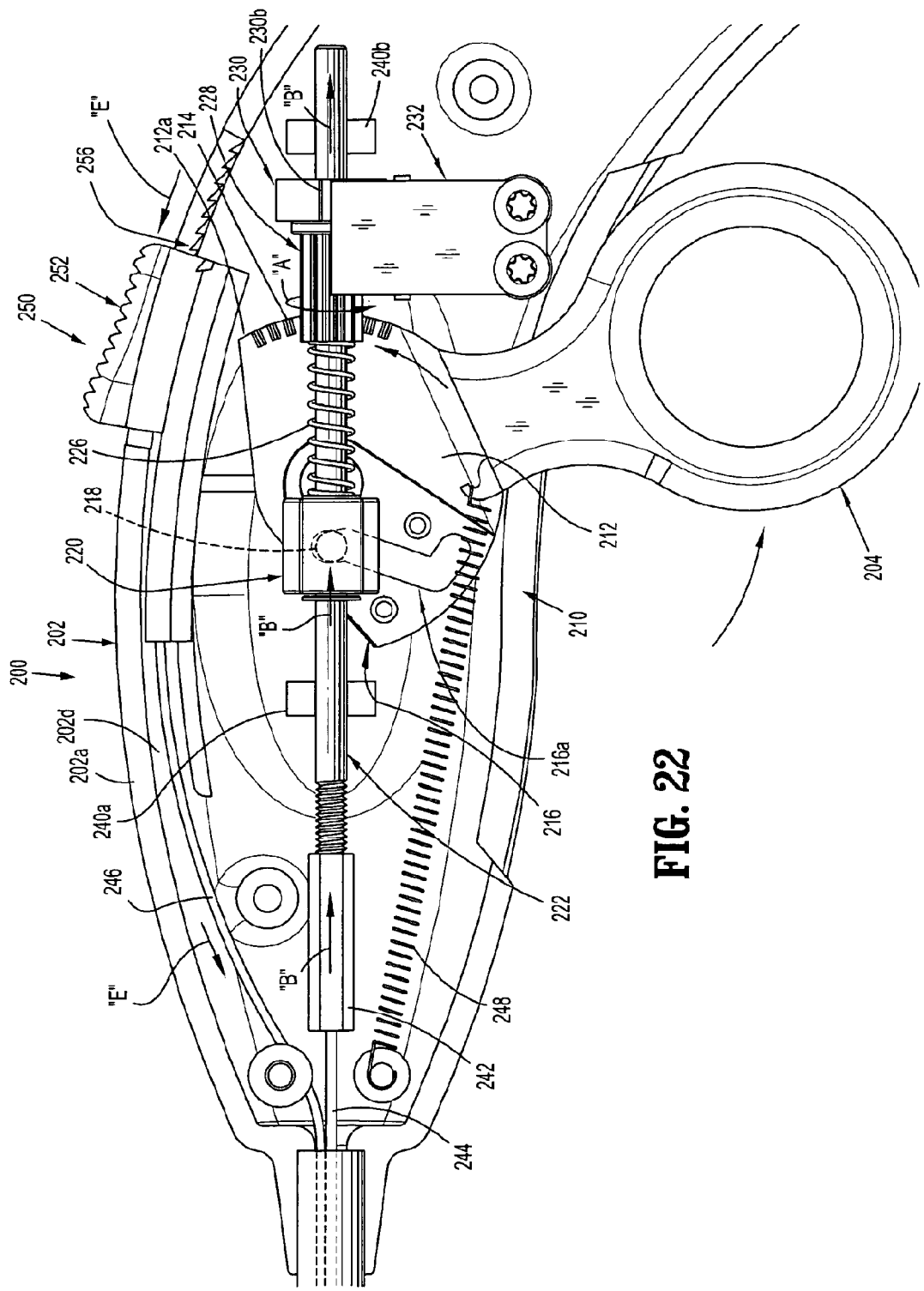
FIG. 22 is a side elevational view of the handle assembly of FIG. 16, illustrating a trigger of the handle assembly in a second position.

Handle assembly 200 includes a trigger 204 operatively supported in housing 202 and extending therefrom. As will be described in greater detail below, trigger 204 is movable between a first un-actuated position, as seen in FIGS. 15-17, and a second actuated position, as seen in FIG. 22. In use, movement of trigger 204 between the first and second positions results in actuation and/or operation of stitching device 100.

Trigger 204 is operatively associated or otherwise connected to an actuation mechanism 210 (see FIG. 20) of handle assembly 200. As will be described in greater detail below, in use, movement of trigger 204 between the first and second positions results in two operations of an end effector.

As seen in FIGS. 16-18, 20, 22 and 23, actuation mechanism 210 includes a trigger plate 212 connected to and extending from trigger 204. Trigger plate 212 defines a gear segment 214 along a proximal or rear edge 212*a* thereof.

Actuation mechanism 210 includes a cam plate 216 fixedly supported or connected to trigger plate 212. Cam plate 216 is secured to trigger plate 212 so as to rotate about a pivot axis "Y" (see FIG. 18) of trigger 204 and trigger plate 212. Cam plate 216 defines a cam slot 216*a* formed therein including a first, second and third section 216*b*, 216*c*, and 216*d* (see FIG. 18), respectively. Cam slot 216*a* has a substantially "S-shaped" configuration. As seen in FIGS. 18 and 20, a cam follower 218 is slidably positioned in cam slot 216*a* of cam plate 216.

Actuation mechanism 210 includes a cam follower block 220 operatively associated with cam plate 216. Follower block 220 pivotably supports cam follower 218 via a pivot pin 218*a* or the like. In use, as will be described in greater detail below, as trigger 240 moved between the first and second positions, cam plate 216 is pivoted about pivot axis "Y" and follower block 220 is displaced along cam slot 216*a* of cam plate 216. As best seen in FIGS. 18 and 20, follower block 220 defines a lumen 220*a* therethrough. Lumen 220*a* of follower block 220 is oriented in a direction orthogonal to pivot axis "Y". In one embodiment, lumen 220*a* of follower block 220 is coaxially disposed on a longitudinal "X" axis of a drive shaft of handle assembly 200.

As seen in FIGS. 16-18, 20, 22 and 23, actuation mechanism 210 includes a drive or actuation shaft 222 extending through and operatively associated with follower block 220. Actuation shaft 222 may be an extension of or may be operation cable 110*a* of stitching device 100. Actuation shaft 222 is axially fixed relative to follower block 220 by a pair of retaining rings 224*a*, 224*b* connected to actuation shaft 222 at a respective location distal and proximal of follower block 220. In this manner, actuation shaft 222 is free to rotate about a longitudinal axis thereof, relative to follower block 220, and moves distally and proximally with a corresponding distal or proximal movement of follower block 220.

Actuation mechanism 210 includes a coil or compression spring 226 disposed on actuation shaft 222 at a location proximal of follower block 220. Actuation mechanism 210 further includes a pinion gear 228 rotatably supported on actuation shaft 222 at a location proximal of spring 226. Pinion gear 228 is positioned on actuation shaft 222 so as to operatively engage and/or mesh with gear segment 214 of trigger plate 212.

Actuation mechanism 210 further includes a toothed wheel 230 fixedly supported on or connected to actuation shaft 222 via a screw or fastener 230*a*. Toothed wheel 230 defines a pair of diametrically opposed teeth 230*b* formed therein or thereon. Toothed wheel 230 is disposed at a location proximal of pinion gear 228 and is in frictional engagement therewith. A pawl 232 is operatively associated with toothed wheel 230 in such a manner so as to permit rotation of toothed wheel 230 in a single direction.

With continued reference to FIGS. 15-13, a method of using and/or operating handle assembly 200 is shown and described. As seen in FIGS. 16 and 17, when trigger 204 is in a first or un-actuated position, cam follower 218 is positioned proximate a distal end of second section 216*c* of cam slot 216*a* of cam plate 216.

As seen in FIG. 22, when trigger 204 is squeezed to a second or fully actuated position, gear segment 214 of trigger plate 212 is pivoted about pivot axis "Y" and actuates (i.e., rotates) pinion gear 228 in a first direction "A". Since pinion gear 228 is rotatably supported on actuation shaft 222, no rotation of actuation shaft 222 is imparted thereto. Also, since pinion gear 228 frictionally engages toothed gear 230, rotation of pinion gear 228 imparts rotation to toothed gear 230. However, as seen in FIGS. 19 and 22, rotation of toothed gear 230, in the direction of arrow "A", is prevented by the interengagement of pawl 232 with a tooth 230*b* of toothed gear 230.

With continued reference to FIG. 22, simultaneously or concomitantly with the rotation of pinion gear 228 in the direction of arrow "A", as trigger 204 is squeezed to a second or fully actuated position, cam follower 218 is caused to be displaced through cam slot 216*a* of cam plate 216. As cam follower 218 is moved through cam slot 216*a*, follower block 220 is caused to be moved in a proximal direction, as indicated by arrow "B". Movement of follower block 220 in the direction of arrow "B" results in the movement of actuation shaft 222 in the direction of arrow "B". Movement of actuation shaft 222 solely in an axial direction is accomplished through uprights or guides 240*a*, 240*b*, located near a distal end and a proximal end of actuation shaft 222.

Movement of actuation shaft 222 in the direction of arrow "B" results in movement of an adjustment screw 242, operatively connected to a distal end of actuation shaft 222, in the direction of arrow "B", which in turn results in movement of a first actuation cable 244 in the direction of arrow "B". Movement of first actuation cable 244, in the direction of arrow "B", may result in a first operation or movement of an end effector (not shown), such as, for example, an approximation or an opening or jaws of the end effector. In an alternative embodiment (not shown), a rigid or substantially rigid rod or shaft may be substituted for actuation cable 244.

Figure 23:
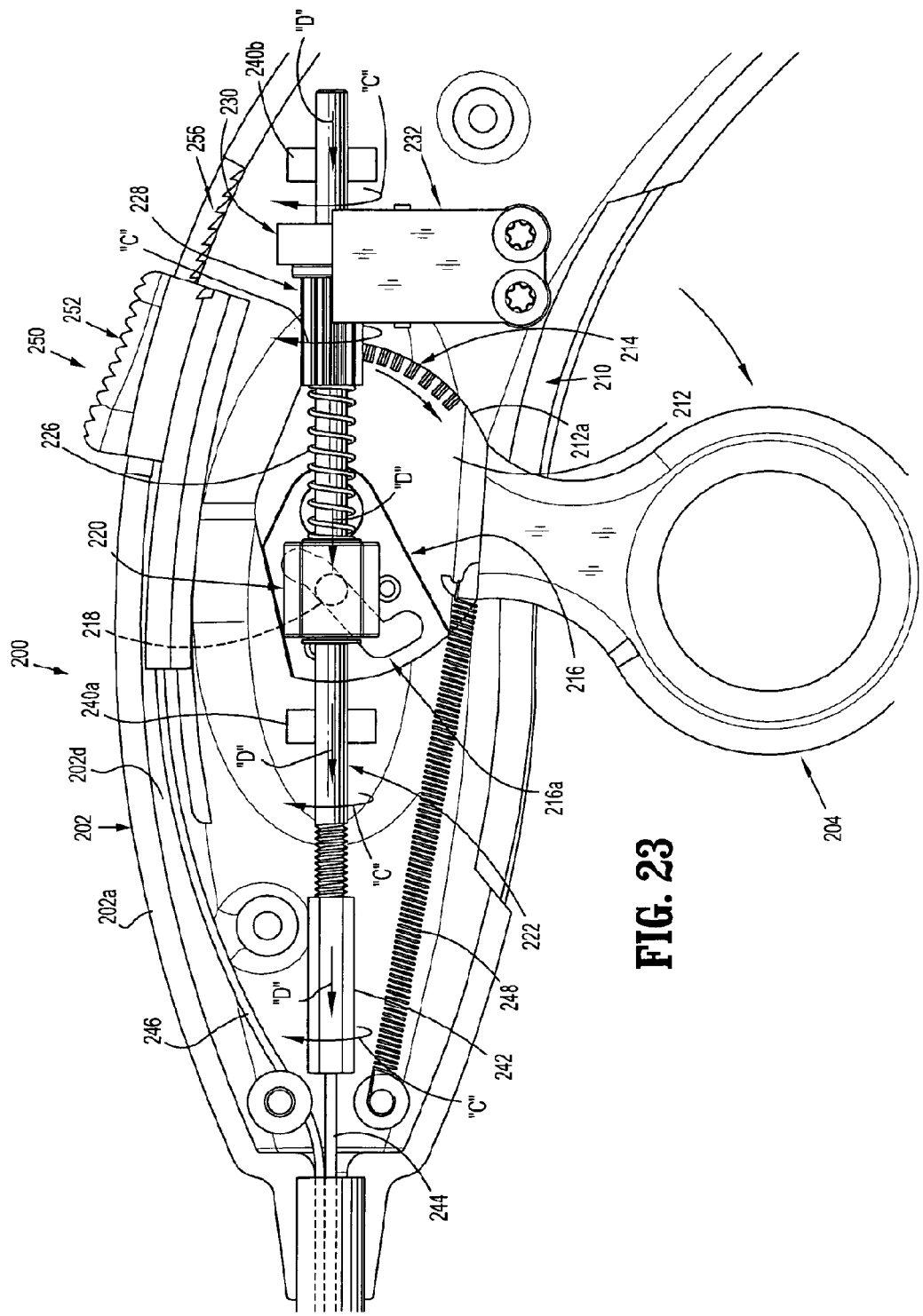
FIG. 23 is a side elevational view of the handle assembly of FIG. 16, illustrating a trigger of the handle assembly in a third position.
Figure 24:
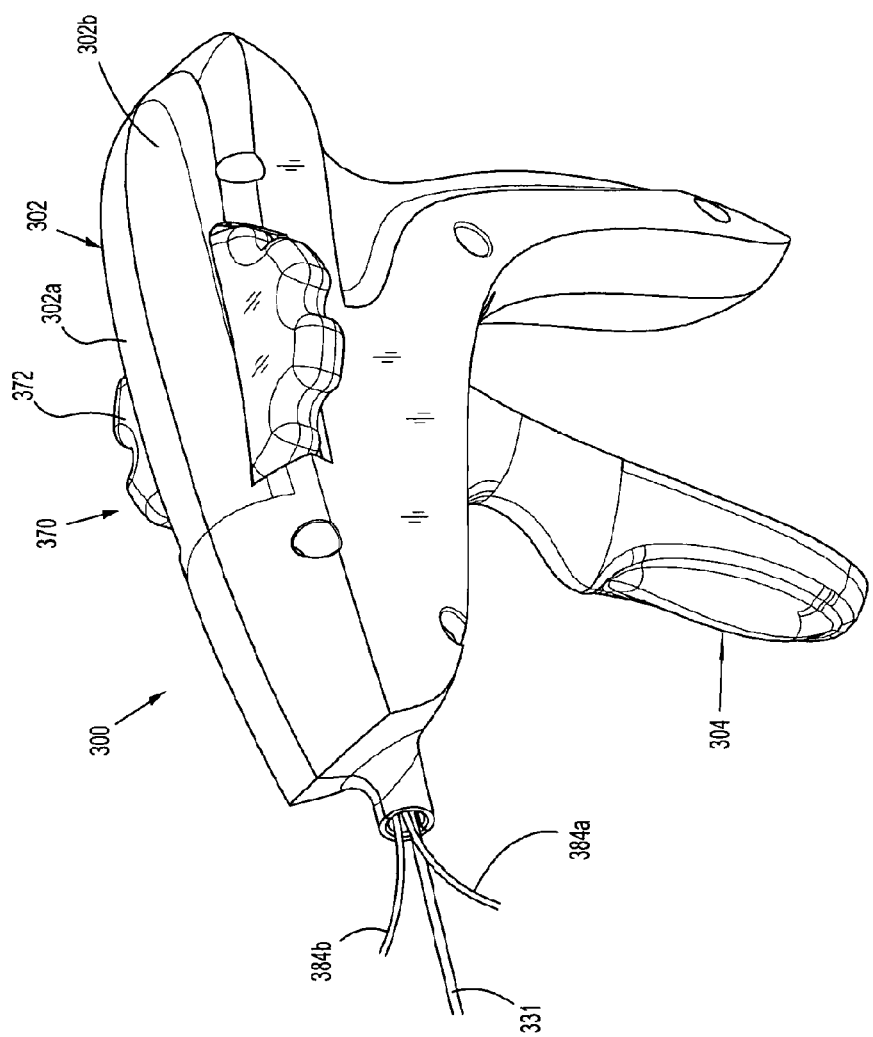
FIG. 24 is a perspective view of a handle assembly according to another embodiment of the present disclosure.

As seen in FIG. 23, upon release of trigger 204 or upon the return of trigger 204 to the first or un-actuated condition, gear segment 214 of trigger plate 212 is pivoted about pivot axis "Y" and actuates (i.e., rotates) pinion gear 228 in a second direction "C", opposite to first direction "A". Since pinion gear 228 frictionally engages toothed gear 230, rotation of pinion gear 228 in the direction of arrow "C" imparts rotation to toothed gear 230. As seen in FIGS. 19 and 23, rotation of toothed gear 230, in the direction of arrow "C", is permitted since pawl 232 does not engage tooth 230*b* of toothed gear 230 but simply slides thereover.

Since toothed gear 230 is keyed to or otherwise fixedly connected to actuation shaft 222, rotation of toothed gear 230 in the direction of arrow "C" also results in rotation of actuation shaft 222, and in turn first actuation cable 244, in the direction of arrow "C". Rotation of first actuation cable 244 in the direction of arrow "C" may result in a second operation or movement of an end effector (not shown).

With continued reference to FIG. 23, simultaneously or concomitantly with the rotation of pinion gear 228 in the direction of arrow "C", as trigger 204 is moved or returned to the first or un-actuated position, cam follower 218 is caused to be displaced through cam slot 216a of cam plate 216. As cam follower 218 is moved through cam slot 216a, follower block 220 is caused to be moved in a distal direction, as indicated by arrow "D". Movement of follower block 220 in the direction of arrow "D" results in the movement of actuation shaft 222 in the direction of arrow "D". Guides 240a, 240b once again solely permit movement of actuation shaft 222 in an axial direction.

Movement of actuation shaft 222 in the direction of arrow "D" results in movement of adjustment screw 242, and in turn first actuation cable 244 in the direction of arrow "D". Movement of first actuation cable 244, in the direction of arrow "D", may result in a third operation or movement of an end effector (not shown), such as, for example, an approximation or an opening or jaws of the end effector.

Return or movement of trigger 204 from the second position to the first position is facilitated by a tension spring 248 or the like operatively connected to and extending between housing 202 and trigger 204.

With continued reference to FIGS. 15-23, handle assembly 200 further includes another actuation mechanism or articulation controller 250. Articulation controller 250 includes a slider 252 slidably supported in tracks 202d formed in housing 202. Slider 252 is biased to a raised position by a biasing member 254 (i.e., spring clip or the like, see FIG. 18). In the raised position, a tooth 252a formed on slider 252 engages with a tooth 256a of a rack 256 formed in housing 202. A second actuation cable 246 extends from slider 252 and out through a distal end of housing 202 to operative engage an end effector (not shown).

In operation, as seen in FIG. 22, as slider 252 is actuated or moved in the direction of arrow "E" (i.e., from a proximal-most to a distal-most position), second actuation cable 246 is also moved in the direction of arrow "E". Movement of second actuation cable in the direction of arrow "E" may result in an operation of an end effector (not shown), such as, for example, an articulation of an end effector in a direction or an approximation or an opening or jaws of the end effector.

In order to move slider 252 in a direction opposite to arrow "E", slider 252 is pressed toward housing 202 to disengage tooth 252a thereof from teeth 256a of rack 256. In this manner, slider 252 is free to be moved from a distal-most position to a proximal-most position.

First and second actuation cables 244 and 246 may be sheathed in a flexible, non-radially expandable, sleeve 247 or the like. Sleeve 247 functions to ensure that first and second actuation cables 244 and 246 solely translate in an axial direction and do not deflect radially outward. Each actuation cable 246, 248 may be fabricated from a suitable material, i.e., stainless steel, capable of transmitting axial and torsional forces.

Turning now to FIGS. 24-37, a handle assembly, in accordance with another embodiment of the present disclosure, for operating, manipulating and/or controlling an endoscopic device, such as stitching device 100, is generally designated as 300. Handle assembly 300 includes a housing 302 having a right-half section 302a and a left-half section 302b joinable to one another by suitable fastening elements (not shown), such as screws.

Figure 35:
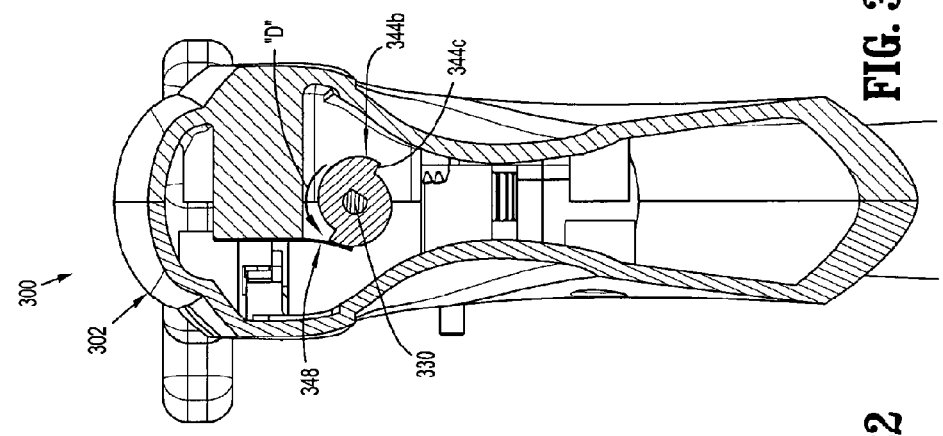
FIG. 35 is a cross-sectional view of the handle assembly of FIGS. 24-27, as taken through 35-35 of FIG. 25, illustrating a second position of the uni-directional pawl assembly.
Figure 33:
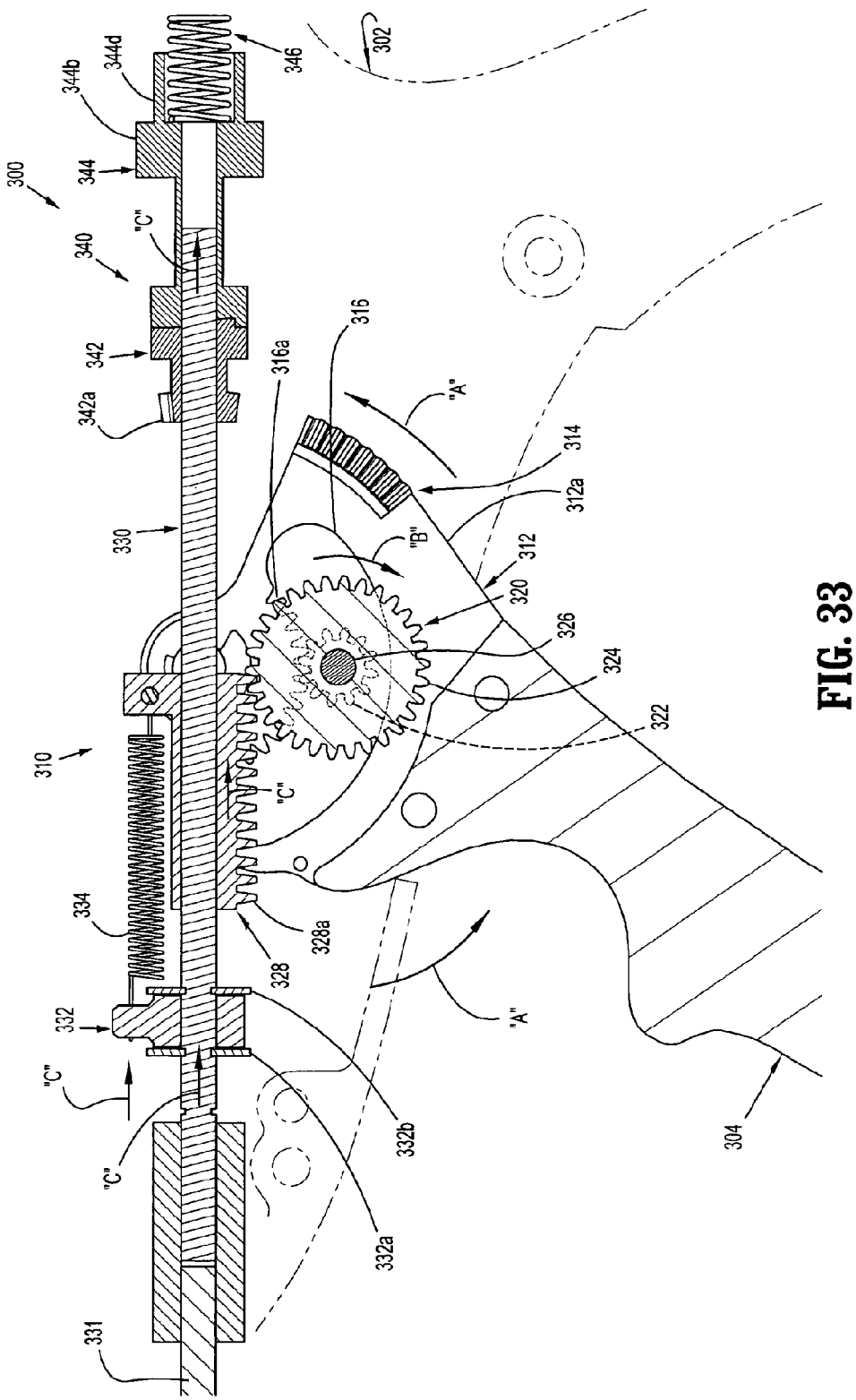
FIG. 33 is a side elevational view of a drive mechanism of the handle assembly of FIGS. 24-27, illustrating the drive mechanism and a trigger of the handle assembly at a first position.
Figure 34:
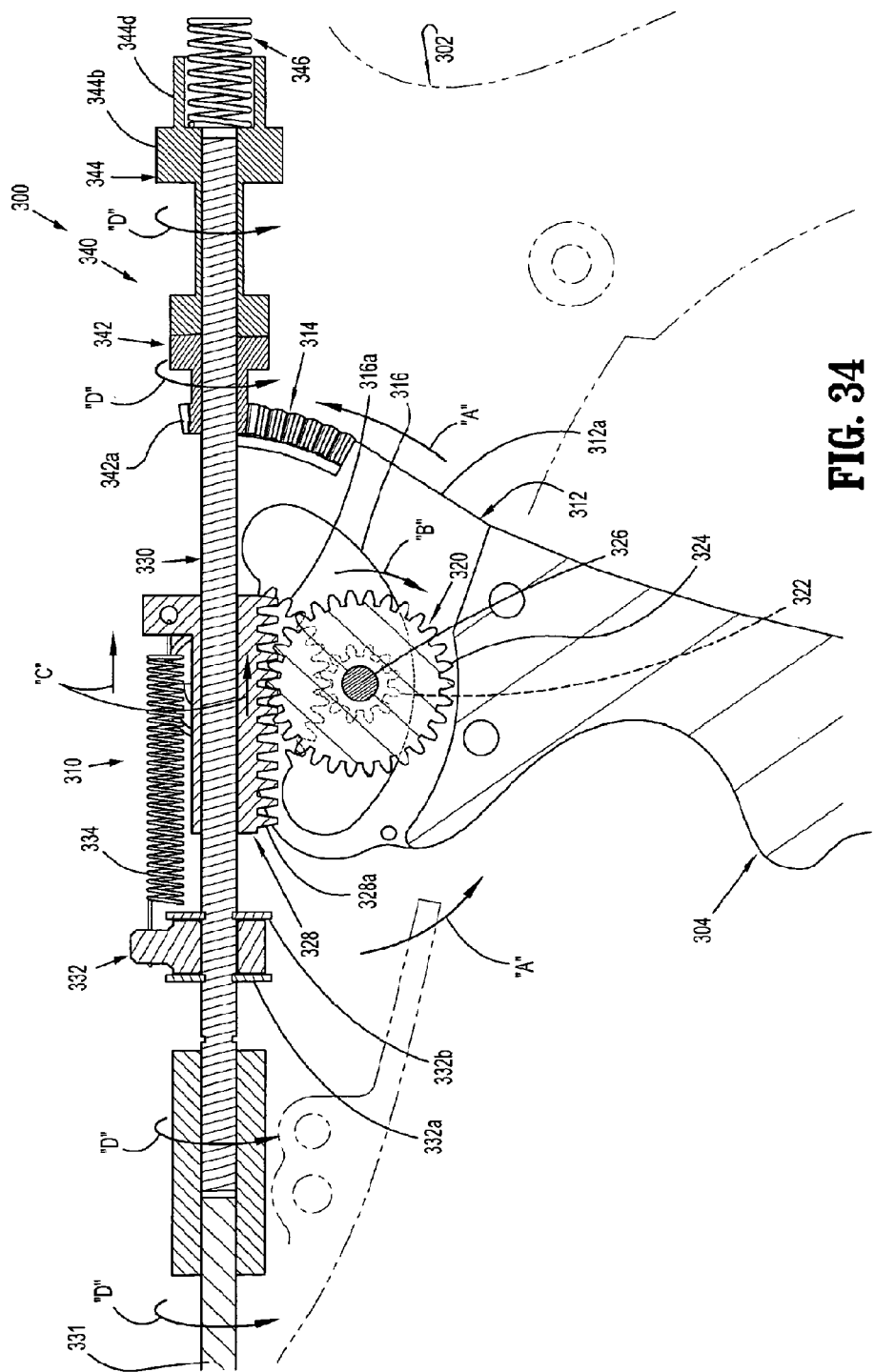
FIG. 34 is a side elevational view of the drive mechanism of FIG. 33, illustrating the drive mechanism and the trigger of the handle assembly at a second position.

Handle assembly 300 includes a trigger 304 operatively supported in housing 302 and extending therefrom. As will be described in greater detail below, trigger 304 is movable between a first un-actuated position, as seen in FIGS. 24-26 and 33, and at least one second actuated position, as seen in FIGS. 34-35. In use, movement of trigger 304 between the first and second positions results in actuation and/or operation of an end effector (not shown).

Trigger 304 is operatively associated or otherwise connected to an actuation mechanism 310 (see FIGS. 25-27 and 33-37) of handle assembly 300. As will be described in greater detail below, in use, movement of trigger 304 between the first and second positions results in two operations of an end effector.

As seen in FIGS. 25-27 and 33-37, actuation mechanism 310 includes a trigger plate 312 connected to and extending from trigger 304. Trigger plate 312 pivotally connects trigger 304 to housing 302. Trigger plate 312 defines a first gear segment 314 along a proximal or rear edge 312a thereof. Trigger plate 312 defines an arcuate slot 316 therein having a second gear segment 316a formed along an upper edge thereof. Slot 316 has a radius of curvature having its center located on a pivot axis "Y" (see FIG. 26) of trigger 304.

A gear set 320 is operatively associated with slot 316 of trigger plate. Gear set 320 includes a first gear 322 configured to mesh with and/or otherwise operatively engage second gear segment 316a of slot 316, and a second gear 324 supported on a common rotational pin 326 as first gear 322. In this manner, as first gear 322 is rotated due to a movement of trigger 304, second gear 324 is simultaneously and/or concomitantly rotated.

Second gear 324 of gear set 320 is configured to mesh with and/or otherwise operatively engage teeth 328 of a rack 328. Rack 328 defines a lumen 328b therethrough. Lumen 328b of rack 328 is oriented in a direction tangential to pivot axis "Y". In one embodiment, lumen 328b of rack 328 is coaxially disposed on a longitudinal "X" axis of an actuation shaft of handle assembly 300.

As seen in FIGS. 25-27 and 33-37, actuation mechanism 310 includes a drive or actuation shaft 330 extending through and operatively associated with rack 328, and a follower block 332 rotatably supported on actuation shaft 330 at a fixed location distal of rack 328. Actuation shaft 330 may be an extension of or may be operation cable 110a of stitching device 100. Actuation shaft 330 is axially translatable and rotatable relative to rack 328. Follower block 332 is axially held in position relative to actuation shaft 330 by a pair of ring clamps 332a, 332b secured to actuation shaft 330 at a location distal and proximal of follower block 332. Rack 328 and follower block 332 are connected to one another by a biasing member 334, i.e., a tension spring, extending therebetween.

Figure 32:
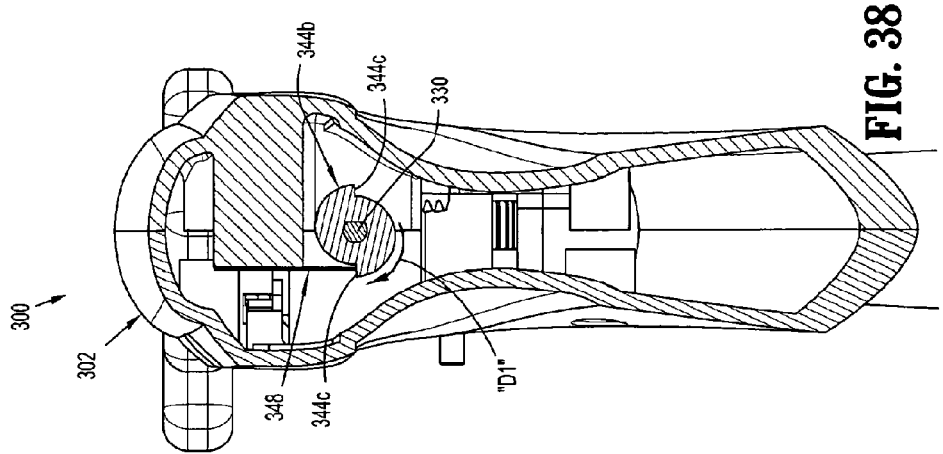
FIG. 32 is a cross-sectional view of the handle assembly of FIGS. 24-27, as taken through 32-32 of FIG. 25, illustrating a first position of a uni-directional pawl assembly.
Figure 38:
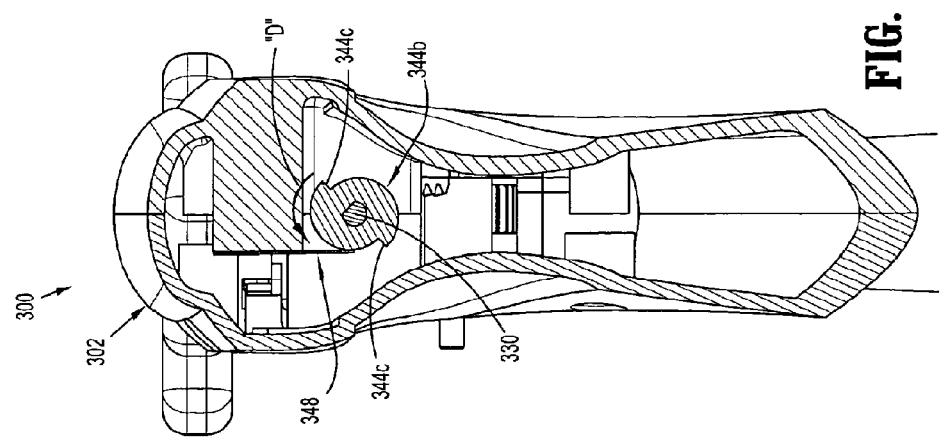
FIG. 38 is a cross-sectional view of the handle assembly of FIGS. 24-27, as taken through 38-38 of FIG. 25, illustrating a third position of the uni-directional pawl assembly.

Actuation mechanism 310 includes a slip-clutch 340 supported on a proximal end of actuation shaft 330. As seen in FIG. 29, slip clutch 340 includes a distal portion 342 having a distal bevel gear 342a configured to mesh with and/or otherwise operatively engage first gear segment 314 of trigger plate 312, and a set of proximally-facing gear teeth 342b. Slip clutch 340 further includes a proximal portion 344 having a set of distally-facing gear teeth 344a configured to mesh with and/or otherwise operatively engage the set of proximally-facing gear teeth 342b of distal portion 342, and a toothed wheel 344b located proximal of the set of distally-facing gear teeth 344a. Toothed wheel 344b defines a pair of diametrically opposed teeth 344c formed therein or thereon. As seen in FIGS. 32, 35 and 38, toothed wheel 344b is keyed to actuation shaft 330 so as to solely enable axial displacement of toothed wheel 344b relative to actuation shaft 344b.

In operation, as will be discussed in greater detail below, the set of distally-facing gear teeth 344a cooperate with the set of proximally-facing gear teeth 342b to impart rotation in a single direction.

Proximal portion 344 of slip-clutch 340 is biased against distal portion 342 of slip-clutch 340 by a biasing member 346, such as, for example, a compression spring or the like, disposed between housing 302 and proximal portion 344 of slip-clutch 340. A pawl 348 is operatively associated with toothed wheel 344b in such a manner so as to permit rotation of toothed wheel 344b in a single direction.

Figure 25:
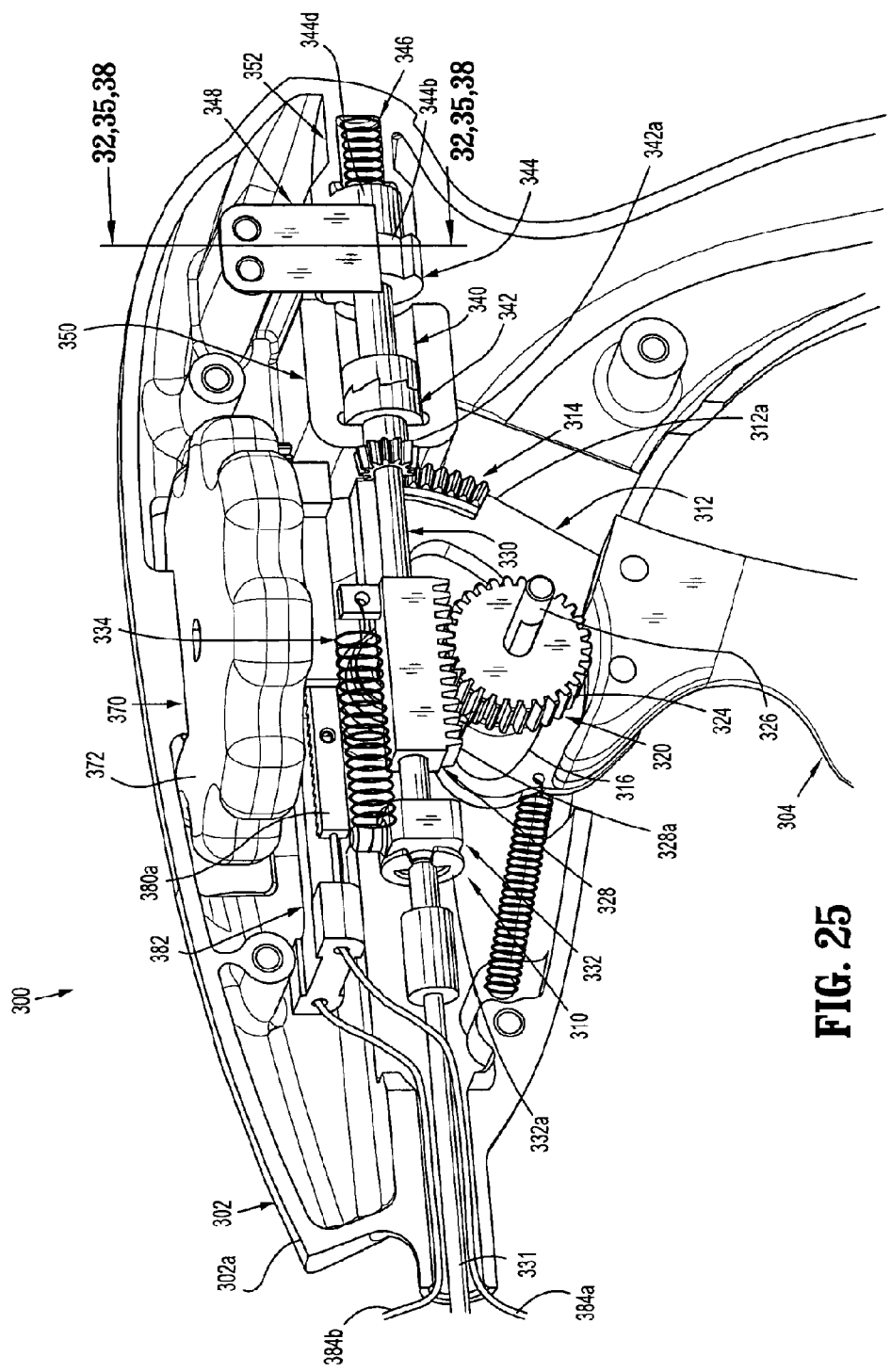
FIG. 25 is a left-side perspective view of the handle assembly of FIG. 24, with a left half-section of the housing removed therefrom.
Figure 26:
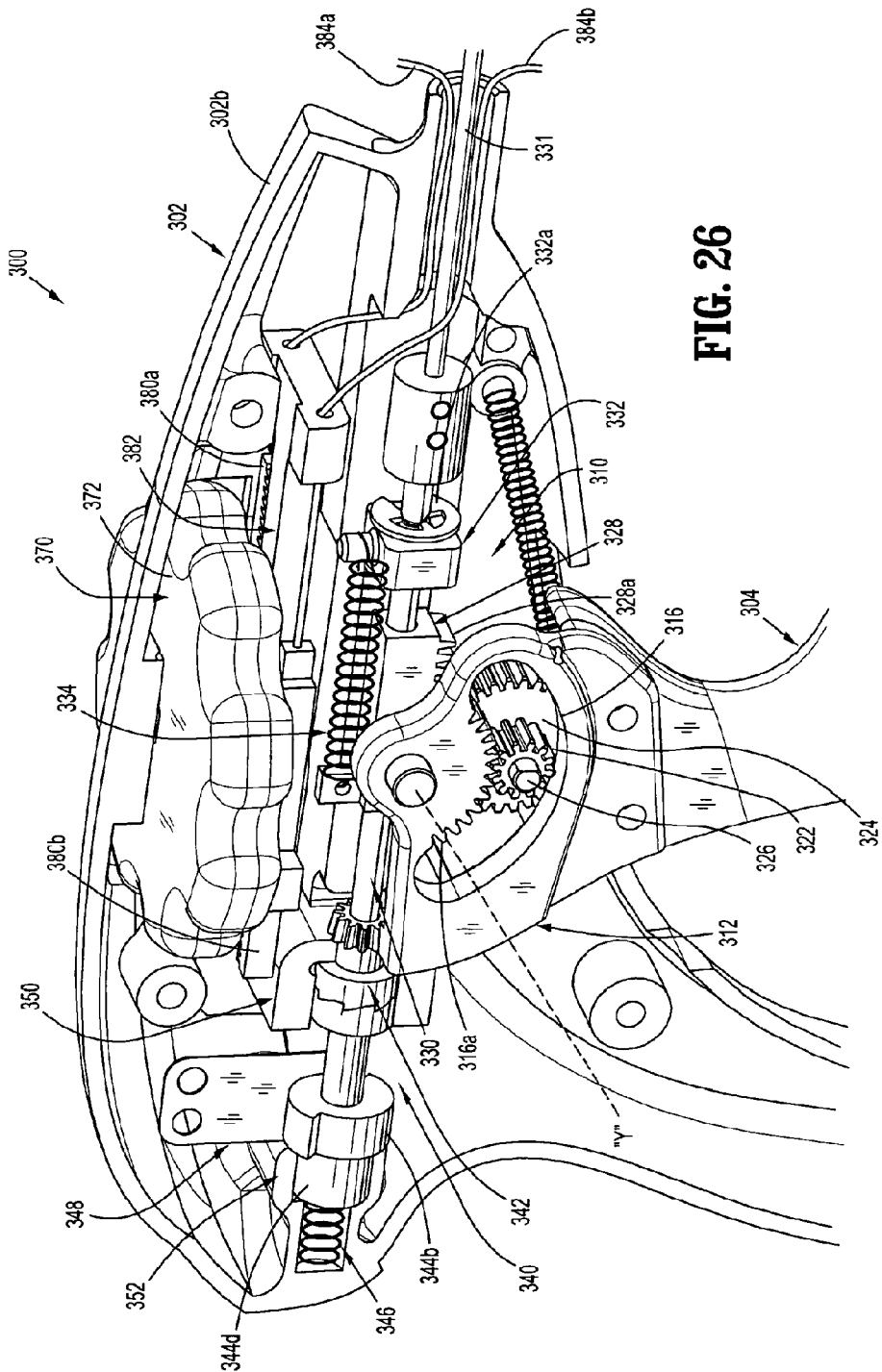
FIG. 26 is a right-side perspective view of the handle assembly of FIG. 24, with a right half-section of the housing removed therefrom.
Figure 27:
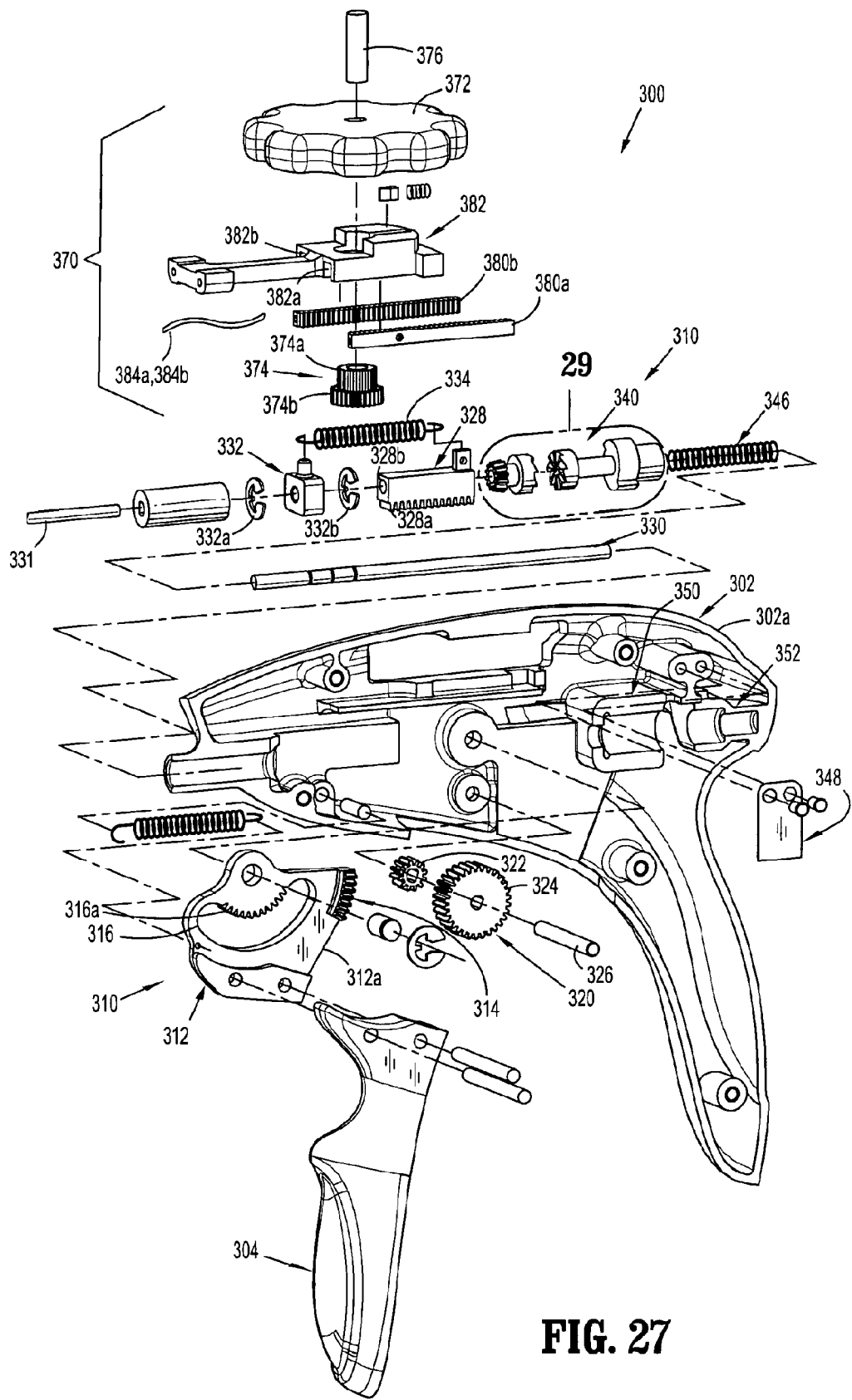
FIG. 27 is an exploded perspective view of the handle assembly of FIGS. 24-26.

As seen in FIGS. 25-27, at least proximally-facing gear teeth 342b of distal portion 342 of slip-clutch 340 is retained in a hub 350 formed in housing 302, and at least a boss 344d, extending proximally from toothed wheel 344b, is retained in a hub 352 formed in housing 302.

With continued reference to FIGS. 24-37, a method of using and/or operating handle assembly 300 is shown and described. As seen in FIG. 33, when trigger 304 is in a first or un-actuated position, rack 328 is at a distal-most position relative to actuation shaft 330 such that a proximal-most tooth 328a thereof meshes with and/or otherwise operatively engages second gear 324 of gear set 320. Also, as seen in FIG. 33, when trigger 304 is in a first or un-actuated position, first gear segment 314 of trigger plate 312 is spaced a distance from bevel gear 342a of distal portion 342 of slip clutch 340.

As seen in FIGS. 33 and 34, as trigger 304 is squeezed or moved to a second or at least partially actuated position, as indicated by arrow "A", second gear segment 316a of slot 316 causes first gear 322 as well as second gear 324 of gear set 320 to rotate in the direction of arrow "B". As first and second gears 322, 324 of gear set 320 are rotated in the "B" direction, second gear 324 causes rack 328 to move in the direction of arrow "C" (i.e., in a proximal direction). As rack 328 is moved proximally, actuation shaft 330 is also moved proximally, in the direction of arrow "C", due to the connection of follower block 332 to rack 330 via biasing member 334. Proximal movement of actuation shaft 330 may result in an operation or movement in an end effector (not shown) connected to a distal end of actuation shaft 330 via an actuation cable 331.

As seen in FIG. 34, as trigger 304 is further squeezed or moved in the direction of arrow "A", first gear segment 314 of trigger plate 312 operatively engages bevel gear 342a of distal portion 342 of slip clutch 340. As trigger 304 is moved in the direction of arrow "A", first gear segment 314 of trigger plate 312 imparts rotation to bevel gear 342a of distal portion 342 of slip clutch 340, in the direction of arrow "D". Rotation of bevel gear 342a of distal portion 342 of slip clutch 340 in turn imparts rotation to proximal portion 344 of slip clutch 340, due to the meshing of respective gear teeth 342b, 344a, which in turn imparts rotation to actuation shaft 330, due to the keying of toothed wheel 344b of proximal portion 344 to actuation shaft 330.

As seen in FIGS. 32 and 35, as toothed wheel 344b of proximal portion 344 of slip clutch 340 is rotated in the direction of arrow "D", pawl 348 rides over and against an outer surface thereof.

Figure 36:
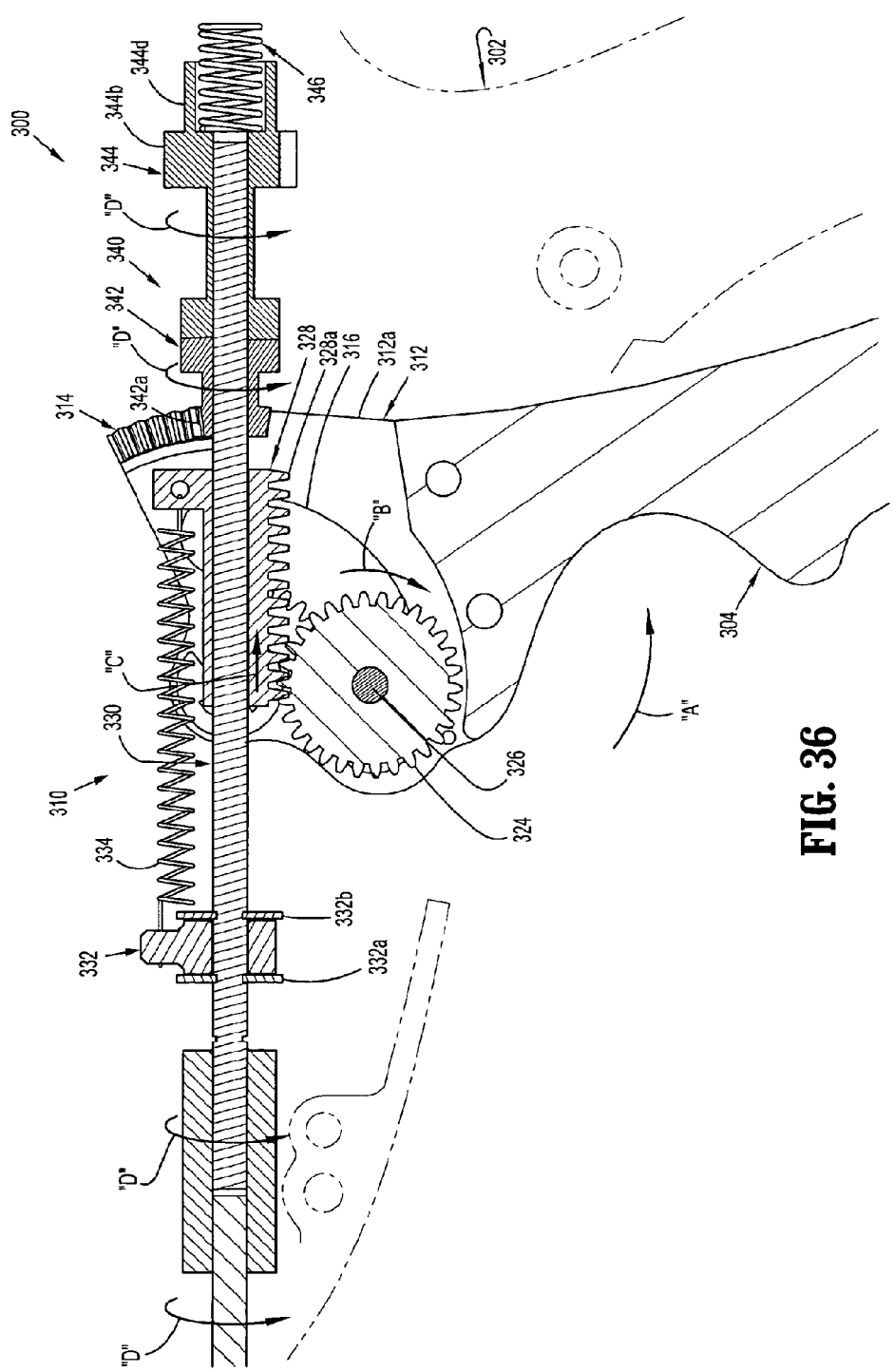
FIG. 36 is a side elevational view of the drive mechanism of FIG. 33, illustrating the drive mechanism and trigger of the handle assembly in a third position.

As seen in FIG. 36, as trigger 304 is further squeezed or moved in the direction of arrow "A", second gear 324 of gear set 320 is further rotated in the direction of arrow "B" causing rack 328 to move further in the direction of arrow "C". However, since actuation shaft 330 has bottomed out (i.e., movement in the direction of arrow "C" is stopped), rack 328 is caused to move in the direction of arrow "C" along actuation shaft 330, and since follower block 332 is axially fixed along actuation shaft 330, biasing member 334 is caused to be elongated. Simultaneously or concomitantly therewith, first gear segment 314 of trigger plate 312 further rotates bevel gear 342a of distal portion 342 of slip clutch 340 in the direction of arrow "D" further rotating actuation shaft 330 in the direction of arrow "D", as described above. Rotation of actuation shaft 330 in the direction of arrow "D" may result in another operation or movement in an end effector (not shown) connected to a distal end of actuation shaft 330 via an actuation cable 331.

Turning now to FIG. 37, as trigger 304 is released or moved in the direction of arrow "A1", opposite to the direction of arrow "A", second gear 324 of gear set 320 is rotated in the direction of arrow "B1", opposite to arrow "B". Second gear 324 is moved in the direction of arrow "B1" either by the movement of trigger 304 in the direction of arrow "A1" or by the movement of rack 328 in the direction of arrow "C1", opposite to the direction of arrow "C". Rack 328 is moved in the direction of arrow "C1" due to the contraction of biasing member 334 approximating rack 328 toward follower block 332. The spring bias of biasing member 334, approximating rack 328 toward follower block 332, facilitates or aids in the return or movement of trigger 304 in the direction of arrow "A1". As rack 328 is moved in the direction of arrow "C1" actuation shaft 330 is also moved in the direction of arrow "C1".

Simultaneously or concomitantly with the movement of trigger 304 in the direction of arrow "A1", first gear segment 314 of trigger plate 312 imparts rotation to bevel gear 342a of distal portion 342 of slip clutch 340 in the direction of arrow "D1", opposite to the direction of arrow "D". As bevel gear 342a of distal portion 342 of slip clutch 340 is rotated in the direction of arrow "D1" gear teeth 342b thereof slips-over and/or against teeth 344a of proximal portion 344 of slip clutch 340, and since proximal portion 344 of slip clutch 340 is cammed in the direction of arrow "D", against the bias of spring 346, no rotation is imparted to proximal portion 344 of slip clutch 340. In turn, since proximal portion 344 of slip clutch 340 does not rotate, no rotation is imparted to actuation shaft 330.

As seen in FIG. 38, as toothed wheel 344b of proximal portion 344 of slip clutch 340 is rotated in the direction of arrow "D1", pawl 348 abuts against a tooth 344c of toothed wheel 344b, preventing rotation of toothed wheel 344b in the direction of arrow "D1" and in turn preventing rotation of actuation shaft 330 in the direction of arrow "D1".

Movement of actuation shaft 330 in the direction of arrow "C1" may result in yet another operation or movement in an end effector (not shown) connected to a distal end of actuation shaft 330 via an actuation cable 331.

Turning now to FIGS. 24-28 and 30-31, handle assembly 300 further includes an articulation mechanism 370 supported on and/or in housing 302. Articulation assembly 370 may be operatively connected to an end effect (not shown) in order to impart articulation to the end effector or any other suitable movement or operation to the end effector.

As seen in FIGS. 24-28 and 30-31, articulation mechanism 370 includes a knob or dial 372 rotatably supported on or in housing 302, and a gear set 374 keyed to and shaving a common rotational axis as dial 372. Gear set 374 includes a first gear 374a and a second gear 374b each supported on and keyed to a pin 376 extending therethrough and through dial 372.

As seen in FIGS. 27 and 28, first gear 374a of gear set 374 operatively engages a locking/feedback member 378 including a finger 378a biased against the teeth of first gear 374a. In operation, as first gear 374a of gear set 374 is rotated, due to a rotation of dial 372, finger 378a rides over the teach of first gear 374a thereby providing the user with tactile and/or audible feedback. Additionally, when dial 372 is not rotated, finger 378a inter-engages with the teeth of first gear 374a to thereby inhibit automatic rotation of dial 372 and thus essentially lock or fix the position of dial 372.

Articulation mechanism 370 further includes a pair of opposed racks 380a, 380b operatively engaged with and on opposed sides of second gear 374b of gear set 374. Each rack 380a, 380b is slidably supported within a respective channel 382a, 382b of a support member 382. Each rack 380a, 380b includes a respective articulation cable 384a, 384b secured thereto. In this manner, during operation, as each rack 380a, 380b is displaced so to is each respective articulation cable 384a, 384b.

In operation, as best seen in FIGS. 30 and 31, as second gear 374b is rotated in a direction of arrow "E", due to the rotation of dial 372, first rack 380a is moved in a proximal direction (i.e., in the direction of arrow "F"), thus displacing first articulation cable 384a in the direction of arrow "F", and second rack 380b is moved in a distal direction (i.e., in the direction of arrow "F1", opposite to arrow "F"), thus displacing second articulation cable 384b in the direction of arrow "F1". It is understood that rotation of dial 372 in an opposite direction and thus rotation of second gear 374b in a direction opposite to arrow "E" will result in movement and/or displacement of racks 380a, 380b and cables 384a, 384b in opposite directions. Rotation of dial 372 thus may impart an operation or movement in an end effector (not shown).

Figure 39:
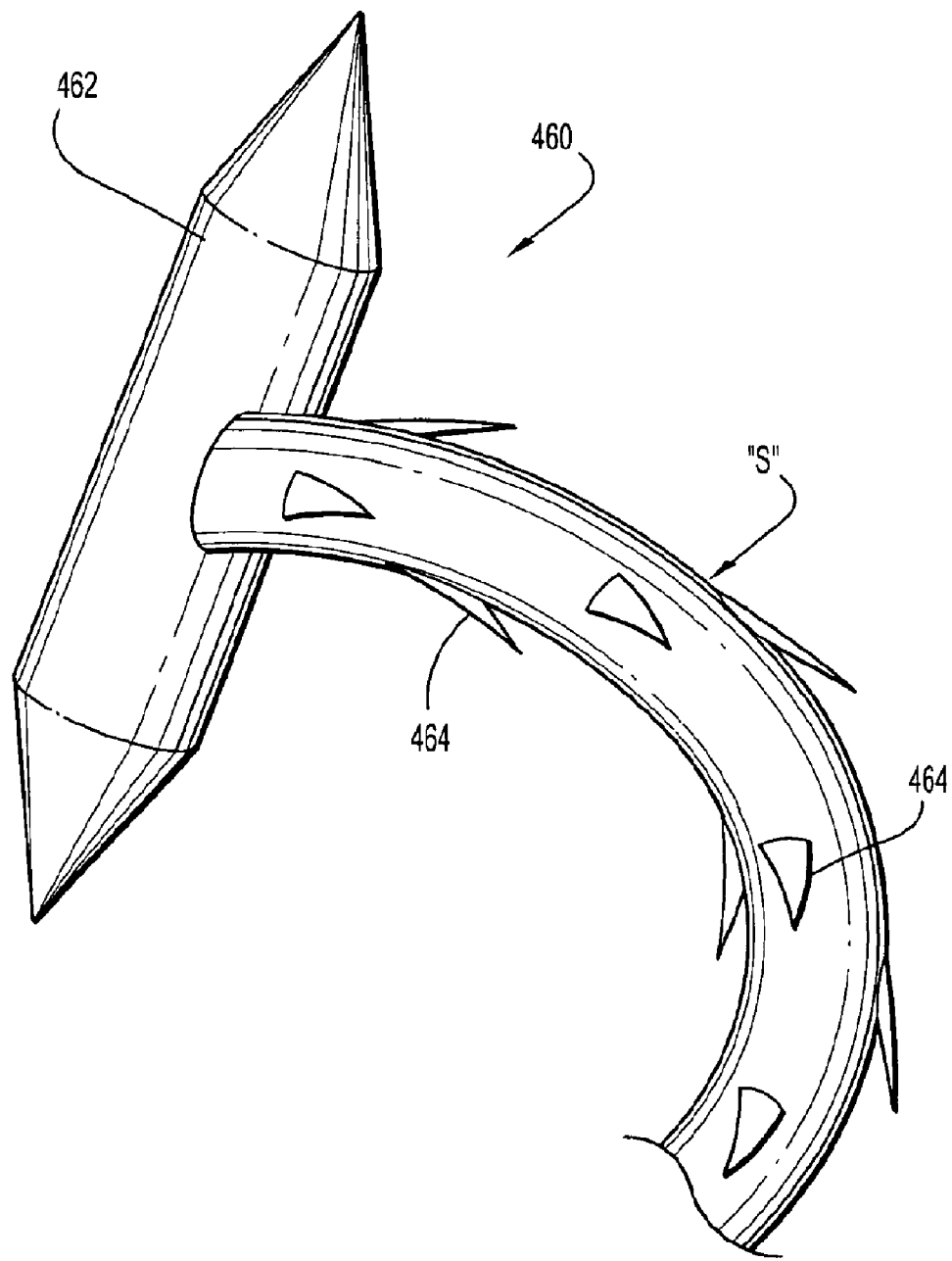
FIG. 39 is a schematic illustration of a suture and needle combination for use in combination with the stitching devices of the present disclosure.

Turning now to FIG. 39, an exemplary suture needle, for use with stitching device 100, is generally shown as 460. Suture needle 460 includes a needle 462 configured and adapted for the intended purpose of operation with stitching device 100 and for performing a surgical suturing procedure, including penetrating tissue and the like.

Suture needle 460 includes a suture "S" secured thereto according to known techniques in the art. Suture "S" of suture needle 460, as well as suture "S" of surgical needle 160, may comprise a one-way or barbed suture "S". Suture "S" includes an elongated body having a plurality of barbs 464 extending therefrom. Barbs 464 are oriented such that barbs 464 cause suture "S" to resist movement in an opposite direction relative to the direction in which barb 464 faces.

Suitable sutures "S" for use in surgical needle 160 or 460, suture needle include, and are not limited to, those sutures described and disclosed in U.S. Pat. No. 3,123,077; U.S. Pat. No. 5,931,855; and U.S. Patent Publication No. 2004/0060409, filed on Sep. 30, 2002, the entire content of each of which being incorporated herein by reference.

While the disclosure has been particularly shown and described with reference to particular embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic stitching device, comprising:
an articulatable neck portion configured and adapted for articulation in at least one direction transverse to a longitudinal axis thereof;
an end effector operatively supported on a distal end of the neck assembly;
an actuating cable operatively coupled with the end effector; and
a suture needle operatively associated with the end effector, wherein the end effector is configured and adapted to selectively engage the suture needle in one of a head assembly and a hub and to axially translate the needle between the head assembly and the hub, wherein axial translation of the actuation cable results in translation of the head assembly and the hub relative to one another, and rotation of the actuation cable results in selective retention of the suture needle in one of the head assembly and the hub.

2. The endoscopic stitching device according to claim 1, wherein the head assembly may be in juxtaposed relation to the hub.

3. The endoscopic stitching device according to claim 1, wherein each of the head assembly and the hub defines a needle retaining recess formed in a tissue contacting surface thereof.

4. The endoscopic stitching device according to claim 1, further comprising a translatable needle engaging holding member supported in each of the head assembly and the hub.

5. The endoscopic stitching device according to claim 4, wherein each holding member includes an advanced position wherein an end of the holding member engages the suture needle when the suture needle is in one of the respective head assembly and hub to thereby secure the suture needle therewith.

6. The endoscopic stitching device according to claim 5, wherein each holding member includes a retracted position wherein the end of the holding member is out of engagement with the suture needle.

7. The endoscopic stitching device according to claim 6, further comprising a cam shaft rotatably supported in the end effector for moving each holding member between the advanced and retracted positions upon a rotation thereof.

8. The endoscopic stitching device according to claim 7, wherein the cam shaft is operatively connected to the head assembly so as to translate the head assembly relative to the hub upon a translation of the cam shaft.

9. The endoscopic stitching device according to claim 8, wherein a proximal end of the cam shaft is fixedly secured to an operation cable.

10. The endoscopic stitching device according to claim 1, further comprising at least one articulation cable slidably extending through the neck portion and having a distal end fixedly connected to one of the end effector and a distal end of the neck portion.

11. The endoscopic stitching device according to claim 10, wherein the articulation cable is disposed along an axis spaced a distance from a neutral bending axis of the neck portion.

12. The endoscopic stitching device according to claim 1, wherein the suture needle includes a length of barbed suture extending therefrom.

13. An endoscopic stitching device, comprising:
an end effector configured and adapted to perform at least a pair of functions, the end effector including a head assembly and a hub in juxtaposed translatable relation relative to one another, each of the head assembly and the hub configured to selectively retain a suture needle; and a single actuation cable operatively connected to the end effector, wherein axial translation of the actuation cable results in translation of the head assembly and the hub relative to one another, and wherein rotation of the actuation cable results in selective retention of the suture needle in a respective one of the head assembly and the hub.

14. The endoscopic stitching device according to claim 13, wherein the actuation cable is capable of translating the head assembly and the hub relative to one another and of causing retention of the suture needle in a respective one of the head assembly and the hub.

15. The endoscopic stitching device according to claim 13, wherein each of the head assembly and the hub defines a needle retaining recess formed in a tissue contacting surface thereof.

16. The endoscopic stitching device according to claim 13, further comprising a radially translatable needle engaging holding member supported in each of the head assembly and the hub, wherein each holding member includes: an advanced position wherein a feature of the holding member engages the suture needle when the suture needle is in one of the respective head assembly and hub, to thereby secure the suture needle therewith; and a retracted position wherein the feature of the holding member is out of engagement with the suture needle.

17. The endoscopic stitching device according to claim 16, wherein rotation of the actuation cable results in movement of each holding pin between the advanced and retracted positions.

18. The endoscopic stitching device according to claim 17, further comprising a cam shaft operatively connected to a distal end of the actuation cable such that rotation of the actuation cable results in rotation of the cam shaft wherein the holding member is operatively engaged with this needle.

19. The endoscopic stitching device according to claim 13, further comprising at least one articulation cable slidably extending through a neck portion and having a distal end fixedly connected to one of the end effector and a distal end of the neck portion.

20. The endoscopic stitching device according to claim 19, wherein the articulation cable is disposed along an axis spaced a distance from a neutral bending axis of the neck portion.

21. The endoscopic stitching device according to claim 13, wherein the suture needle includes a length of barbed suture extending therefrom.

* * * * *